(12) United States Patent
Coates et al.

(10) Patent No.: US 9,493,397 B2
(45) Date of Patent: Nov. 15, 2016

(54) IONOMERS AND METHODS OF MAKING SAME AND USES THEREOF

(75) Inventors: Geoffrey W. Coates, Lansing, NY (US); Henry A. Kostalik, IV, Minneapolis, MN (US); Timothy J. Clark, Kingston (CA); Nicholas J. Robertson, Ashland, WI (US)

(73) Assignee: Cornell University, Ithaca, NY (US)

( * ) Notice: Subject to any disclaimer, the term of this patent is extended or adjusted under 35 U.S.C. 154(b) by 644 days.

(21) Appl. No.: 13/322,306

(22) PCT Filed: May 31, 2010

(86) PCT No.: PCT/US2010/036791
§ 371 (c)(1),
(2), (4) Date: Feb. 10, 2012

(87) PCT Pub. No.: WO2010/138958
PCT Pub. Date: Dec. 2, 2010

(65) Prior Publication Data
US 2013/0137011 A1    May 30, 2013

Related U.S. Application Data

(60) Provisional application No. 61/213,327, filed on May 29, 2009, provisional application No. 61/218,265, filed on Jun. 18, 2009.

(51) Int. Cl.
*C07C 211/63* (2006.01)
*H01M 8/10* (2016.01)

(52) U.S. Cl.
CPC .......... *C07C 211/63* (2013.01); *H01M 8/103* (2013.01); *H01M 8/1023* (2013.01); *C07C 2101/18* (2013.01); *C07C 2102/42* (2013.01); *H01M 8/1011* (2013.01); *Y02E 60/523* (2013.01)

(58) Field of Classification Search
USPC .......................................... 429/492; 564/281
See application file for complete search history.

(56) References Cited

U.S. PATENT DOCUMENTS

| 4,840,982 | A | 6/1989 | Campbell et al. |
| 4,975,172 | A | 12/1990 | Yeager et al. |
| 2007/0265174 | A1* | 11/2007 | Schlenoff ...................... 508/106 |
| 2008/0051281 | A1* | 2/2008 | Dressick et al. ............. 502/101 |
| 2012/0028168 | A1* | 2/2012 | Shinohara ............. H01M 6/166 429/499 |

(Continued)

FOREIGN PATENT DOCUMENTS

WO   WO-2010/138958 A2 * 12/2010

OTHER PUBLICATIONS

Kim, Young-Hoon, et al., Adsorption of a Cationic Polyacrylamide onto the Surface of a Nafion Ionomer Membrane, Macromolecules, vol. 34, No. 21, 2001, pp. 7489-7495.

(Continued)

*Primary Examiner* — Peter D Mulcahy
*Assistant Examiner* — Henry Hu
(74) *Attorney, Agent, or Firm* — Hodgson Russ LLP

(57) ABSTRACT

Ionomers comprising ionic groups such as, for example, tetraalkylammonium groups and methods of making such ionomers. For example, the ionomers can be produced by ring opening metathesis polymerization of alkene-containing monomers with tetraalkylammonium groups and, optionally, alkene-containing monomers without tetraalkylammonium groups. The ionomers can be used in applications such as, for example, fuel cell applications.

22 Claims, 16 Drawing Sheets

(56) References Cited

U.S. PATENT DOCUMENTS

2012/0148773 A1* 6/2012 Parent ............... B01J 39/185
428/36.9
2013/0296499 A1* 11/2013 Coates ............... H01M 8/0291
525/331.4
2014/0120431 A1* 5/2014 Roelofs ............... H01M 8/1058
429/408

OTHER PUBLICATIONS

Parent, J. Scott, et al., Synthesis and Characterization of Isobutylene-based Ammonium and Phosphonium Bromide Ionomers, Macromolecules, vol. 37, No. 20, 2004, pp. 7477-7483.

* cited by examiner

| Measurement | 2:1 DCPC | 1:1 DCPD |
|---|---|---|
| IEC (mmol OH$^-$/g)[a] | 1.0 | 1.4 |
| % Swelling in methanol[b] | 1.7 | n.d.[c] |
| Tensile stress at break (MPa)[d] | 16 ± 6 | 2.3 ± 0.5 |
| % Tensile strain at break[d] | 7.2 ± 3 | 26 ± 3 |
| $\sigma_{20}$ (mS/cm)[e] | 14 ± 2 | 18 ± 2 |
| $\sigma_{50}$ (mS/cm)[e] | 21 ± 4 | 28 ± 3 |

| Molar Ratio of M:DCPD | Conductivity at 20°C (mS/cm) | Conductivity at 50°C (mS/cm) |
|---|---|---|
| 1:2 | 14 | 21 |
| 1:1 | 18 | 28 |
| 2:1 | Swollen hydrogel | Swollen hydrogel |

| Counter Ion | Conductivity (mS/cm) | |
| --- | --- | --- |
| | 22°C | 50°C |
| Br⁻ | 1.8 ± 0.4 | 6.1 ± 0.5 |
| Cl⁻ | 10.0 ± 0.2 | 26.4 ± 0.6 |
| $HCO_3^-$ | 8.9 ± 0.7 | 22 ± 1 |
| $CO_3^{2-}$ | 14 ± 1 | 28 ± 1 |
| OH⁻ | 68.7 ± 0.8 | 111 ± 4 |

| Atom | ¹H shift (ppm) | ¹³C shift (ppm) |
|---|---|---|
| 1 | 7.58 | 133.84 |
| 2 | N.A. | 129.67 |
| 3 | 4.67/4.65 | 69.99 |
| 4 | 3.02 | 51.02 |
| 5 | 3.03 | 50.86 |
| 6 | 3.34 | 74.37 |
| 7 | 1.13 | 26.32 |
| 8 | N.A. | 39.97 |
| 9 | 1.51/1.40 | 33.78 |
| 10 | 1.44/1.37 | 23.18 |
| 11 | 2.14/1.92 | 23.57 |
| 12 | 5.25 | 125.03 |
| 13 | 5.43 | 131.05 |
| 14 | 2.05 | 25.20 |
| 15 | 1.88/1.59 | 36.75 |

| Ratio of COE:1 | Amount of COE (μL, mmol) | Conductivity[a] (mS/cm) | Conductivity[a] (mS/cm) |
| --- | --- | --- | --- |
| 1:1 | 20.0, 0.153 | n.a.[b] | n.a.[b] |
| 1.5:1 | 30.0, 0.230 | 69.1 | 69.3 |
| 2:1 | 40.0, 0.307 | 64.9 | 64.3 |
| 2.5:1 | 50.0, 0.384 | 59.2 | 28.7 |
| 3:1 | 60.0, 0.461 | 55.1 | 52.9 |

Figure 14

| Total olefin:catalyst | Amount of Catalyst (μg, mmol) | Conductivity[a] (mS/cm) | Conductivity[a] (mS/cm) |
| --- | --- | --- | --- |
| 202:1 | 2.7, 3.2 | n.a.[b] | n.a.[b] |
| 133:1 | 4.1, 4.8 | n.a.[b] | n.a.[b] |
| 114:1 | 4.8, 5.7 | 59.7 | 60.4 |
| 100:1 | 5.4, 6.4 | 64.9 | 64.3 |
| 85:1 | 6.4, 7.5 | 59.8 | 58.0 |
| 67:1 | 8.1, 9.5 | 56.1 | 54.8 |
| 50:1 | 10.8, 12.7 | 51.0 | 51.4 |

Figure 15

| COE:1 | Tensile Stress at Break (MPa) | Error (MPa) |
| --- | --- | --- |
| 1.5:1 | 15.2 | ± 4.2 |
| 2:1 | 17.3 | ± 4.2 |
| 2.5:1 | 16.8 | ± 3.0 |
| 3:1 | 13.4 | ± 3.1 |

Figure 16

| Moles of Olefin:Catalyst | Tensile Stress at Break (MPa) | Error (MPa) |
| --- | --- | --- |
| 114:1 | 8.9 | ± 2.6 |
| 100:1 | 17.3 | ± 4.2 |
| 85:1 | 18.2 | ± 3.7 |
| 67:1 | 19.6 | ± 2.2 |
| 50:1 | 27.1 | ± 2.4 |

Figure 17

| Measurement | AAEM-29 | AAEM-33 |
|---|---|---|
| mol % 1[a] | 29 | 33 |
| IEC (mmol $OH^-$/g $I^-$)[b] | 1.29 ± 0.08 | 1.50 ± 0.07 |
| % Water uptake[c] | 97 ± 10 | 132 ± 10 |
| Tensile Strength at break (MPa)[d] | 9 ± 2 | 6 ± 1 |
| % Strain at break[d] | 170 ± 40 | 130 ± 40 |
| $OH^-$ $\sigma_{20}$ (mS/cm)[e] | 40 ± 2 | 48 ± 3 |
| $OH^-$ $\sigma_{50}$ (mS/cm)[e] | 59 ± 2 | 65 ± 3 |
| $CO_3^{2-}$ $\sigma_{20}$ (mS/cm)[f] | 12 ± 1 | 13 ± 1 |
| $CO_3^{2-}$ $\sigma_{50}$ (mS/cm)[f] | 29 ± 3 | 30 ± 2 |

Figure 22

| Solvent | 50 vol% in water | Pure Solvent |
|---|---|---|
| Water | N/A | - |
| Methanol | - | - |
| Ethanol | - | ± |
| n-Propanol | + | + |
| Acetone | - | - |
| Tetrahydrofuran | - | - |

Figure 23

| Solvent | 50 vol% in water | Pure Solvent |
|---|---|---|
| Water | N/A | - |
| Methanol | - | ± |
| Ethanol | - | ± |
| n-Propanol | + | + |
| Acetone | - | - |
| Tetrahydrofuran | - | - |

Figure 24

IONOMERS AND METHODS OF MAKING SAME AND USES THEREOF

CROSS-REFERENCE TO RELATED APPLICATIONS

This application claims priority to U.S. provisional patent application Nos. 61/213,327, filed May 29, 2009, and 61/218,265, filed Jun. 18, 2009, the disclosures of which are incorporated herein by reference.

STATEMENT REGARDING FEDERALLY SPONSORED RESEARCH

This invention was made with government support under contract no. DE-FG02-03ER46072 awarded by the Department of Energy. The government has certain rights in the invention.

FIELD OF THE INVENTION

The present invention generally relates to ionomers and methods of making the same. More particularly, the present invention relates to ionomers for use in applications such as fuel cells.

BACKGROUND OF THE INVENTION

Fuel cells are devices that convert the chemical energy stored in a fuel directly into electricity and could potentially serve as a highly efficient and environmentally sustainable power generation technology for stationary and mobile applications. Fuel cells are promising energy conversion devices; however, improving their performance and enhancing their durability remain significant challenges. Increasing the ionic conductivity and mechanical stability of solid polymer electrolyte membranes to achieve higher operating efficiencies are important goals. Within a fuel cell, the polymer electrolyte membrane, which acts as a barrier between the fuel and oxidant streams and simultaneously serves as the ion conducting medium between the anode and cathode, and as a result is a central, and often performance-limiting component of the fuel cell. Many low temperature (e.g., less than 100° C.) fuel cells employ a proton exchange membrane (PEM) as the electrolyte. The most common polymer electrolyte membrane fuel cells operate under acidic conditions and are therefore proton conducting. Nafion®, a PEM, has dominated the field due its processability, chemical and thermal stability, and proton conductivity (when properly hydrated). However, the use of these membranes is limited to acidic conditions and requires substantial dilution of carbon-based fuels (e.g., methanol) along with thicker (less efficient and more costly) membranes to prevent uncontrollable membrane swelling and fuel crossover. Although PEM fuel cells can perform well, they rely almost exclusively on platinum, a very expensive and scarce noble metal.

A significant advantage of alkaline fuel cells (AFCs) over their acidic counterparts is greatly improved oxygen reduction kinetics as well as better fuel oxidation kinetics. These improvements can lead to higher efficiencies and enable the use of non-precious metal catalysts, greatly reducing the cost of the device. Indeed, hydrogen fueled AFCs can outperform all known low temperature (e.g., less than 200° C.) fuel cells. However, AFCs have traditionally employed liquid alkaline electrolytes containing metal hydroxides (e.g., potassium hydroxide) that react with $CO_2$ (present in oxidant stream or fuel oxidation product when using carbon-based fuels) to form metal bicarbonates and subsequently carbonate salts. If sufficiently high levels of these salts are formed, they can precipitate out of solution decreasing electrolyte conductivity and eventually obstructing electrode pores, both of which compromise power output.

A significant advantage of alkaline fuel cells (AFCs) over their acidic counterparts is greatly improved oxygen reduction kinetics as well as better fuel oxidation kinetics. These improvements can lead to higher efficiencies and enable the use of non-precious metal catalysts, greatly reducing the cost of the device. Indeed, hydrogen fueled AFCs can outperform all known low temperature (e.g., less than 200° C.) fuel cells. However, AFCs have traditionally employed liquid alkaline electrolytes containing metal hydroxides (e.g. potassium hydroxide) that react with $CO_2$ (present in oxidant stream or fuel oxidation product when using carbon-based fuels) to form metal bicarbonates and subsequently carbonate salts. If sufficiently high levels of these salts are formed, they can precipitate out of solution decreasing electrolyte conductivity and eventually obstructing electrode pores, both of which compromise power output.

Based on the foregoing, there exists an ongoing and unmet need for conductive and solvent processable ionomers, which can be used as an AAEM.

BRIEF SUMMARY OF THE INVENTION

In one aspect, the present invention provides an ionomer comprising ionic strained olefin monomer (ISOM) units and optionally random or sequentially placed strained olefin monomer (SOM) units, having the following structure:

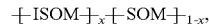

where the ISOM and SOM units are connected by carbon-carbon single bonds and/or carbon-carbon double bonds. The ISOM unit has a non-aromatic hydrocarbon backbone and comprises one or more tetraalkylammonium groups connected to the backbone by an aliphatic polyatomic linkage, and any carbon atoms in the beta position relative to an ammonium nitrogen do not bear hydrogen substituents. The SOM unit is a non-aromatic hydrocarbon unit. The value of x can be from 0.05 to 1.0. The number average molecular weight of the ionomer, Mn, is from 5,000 to 1,000,000 g/mol and/or the weight average molecular weight of the ionomer, Mw, is from 5,000 to 2,000,000 g/mol.

In one embodiment, the end groups of the ionomer can be =$CH_2$, =CHR (where R can be $CH_2$W where W is H, alkyl, halide, hydroxide or acetate), =CHPh, —$CH_3$, —$CH_2$R (where R can be $CH_2$W where W is H, alkyl, halide, hydroxide or acetate) or —$CH_2$Ph.

In various embodiments, the ISOM and SOM units are connected by a carbon-carbon double bond and the ionomer has the following structures:

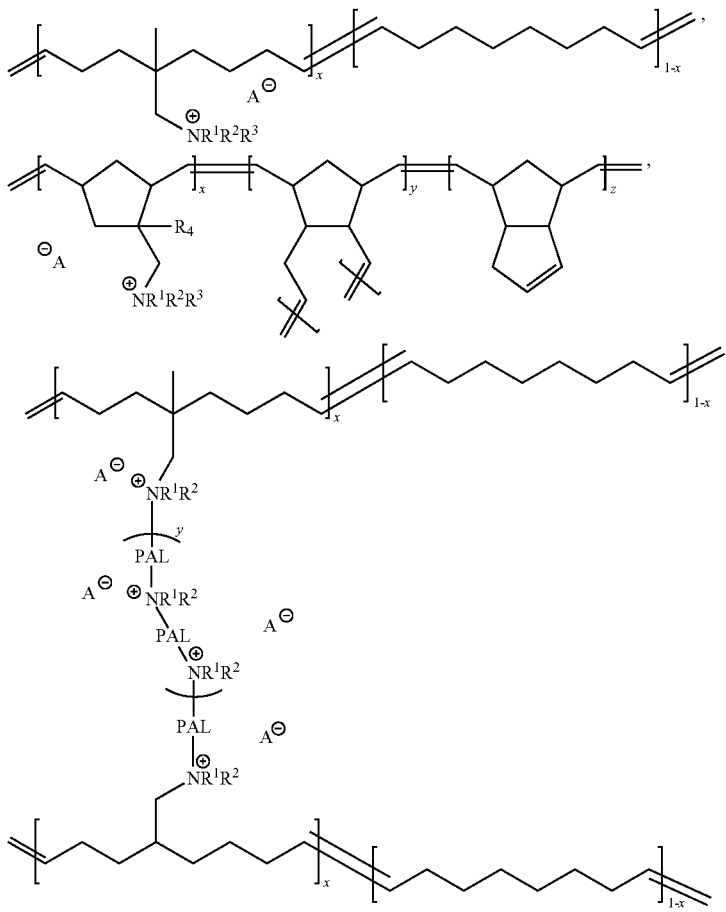

where $R^1$, $R^2$ and $R^3$ are each, independently, a $C_1$ to $C_{20}$ group, and if the $C_1$ to $C_{20}$ group has a carbon in the beta position relative to the ammonium nitrogen atom then the beta carbon of the $C_1$ to $C_{20}$ group does not have a hydrogen substituent. The counter anion, $A^-$, is selected from halide, hydroxide, hexafluorophosphate, borate, carbonate, bicarbonate and carboxylate. The value of x is from 0.05 to 1.0. Each PAL, independently, comprises a $C_1$ to $C_{20}$ group (as described above for $R^1$, $R^2$ and $R^3$). The value of y is from 0 to 20.

In various embodiments, the ISOM and SOM units are connected by a carbon-carbon single bond and the ionomer has the following structure:

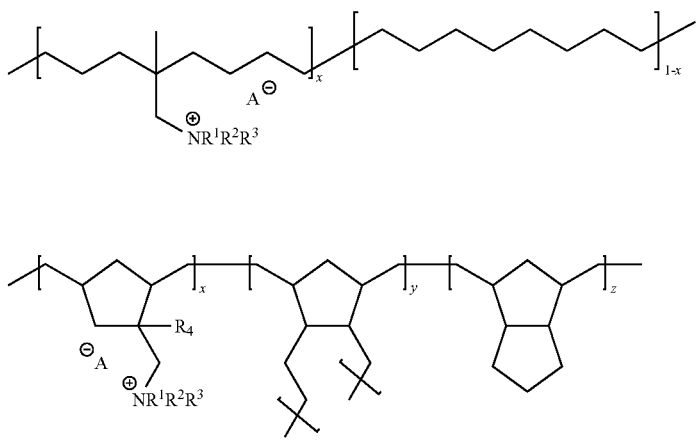

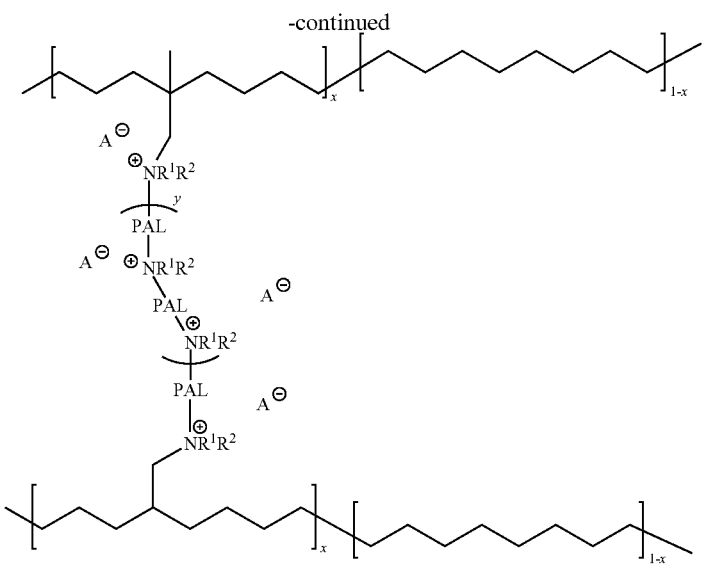

where $R^1$, $R^2$ and $R^3$ are each, independently, a $C_1$ to $C_{20}$ group, and if the $C_1$ to $C_{20}$ group has a carbon in the beta position relative to the ammonium nitrogen atom then the beta carbon of the $C_1$ to $C_{20}$ group does not have a hydrogen substituent. The counter anion, $A^-$, is selected from halide, hydroxide, hexafluorophosphate, borate, carbonate, bicarbonate and carboxylate. The value of x is from 0.05 to 1. Each PAL, independently, comprises a $C_1$ to $C_{20}$ group (as described above for $R^1$, $R^2$ and $R^3$). The value of y is from 0 to 20.

In one aspect, an ionomer of the present invention is synthesized using a transition metal alkene polymerization catalyst (e.g., ring opening polymerization). In one embodiment, the ROMP synthesis of the ionomer is carried out using a ruthenium-based metathesis catalyst. In one embodiment, the ionomer is synthesized by a ring-opening methathesis polymerization (ROMP) carried out using a monomer comprising at least one tetraalkylammonium group having the following structure:

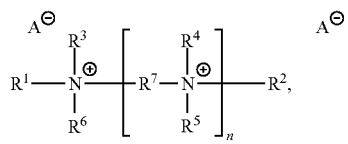

where $R^1$ is a $C_4$ to $C_{20}$ cycloalkenyl group and the carbon in the beta position relative to the ammonium nitrogen does not have a hydrogen substituent. $R^2$, $R^3$, $R^4$, $R^5$ and $R^6$ are, independently, a $C_1$ to $C_{20}$ group, wherein if the $C_1$ to $C_{20}$ group has a carbon in the beta position relative to the ammonium nitrogen atom then the beta carbon of the $C_1$ to $C_{20}$ group does not have a hydrogen substituent. Each $R^7$ is independently a $C_1$ to $C_{20}$ group and if the $C_1$ to $C_{20}$ group has a carbon in the beta position relative to the ammonium nitrogen atom then the beta carbon of the $C_1$ to $C_{20}$ group does not have a hydrogen substituent. The counter ion, $A^-$, is selected from halide, hydroxide, hexafluorophosphate, borate, carbonate, bicarbonate and carboxylate. The value of n is from 0 to 20. In various embodiments, the monomer is selected from the following structures:

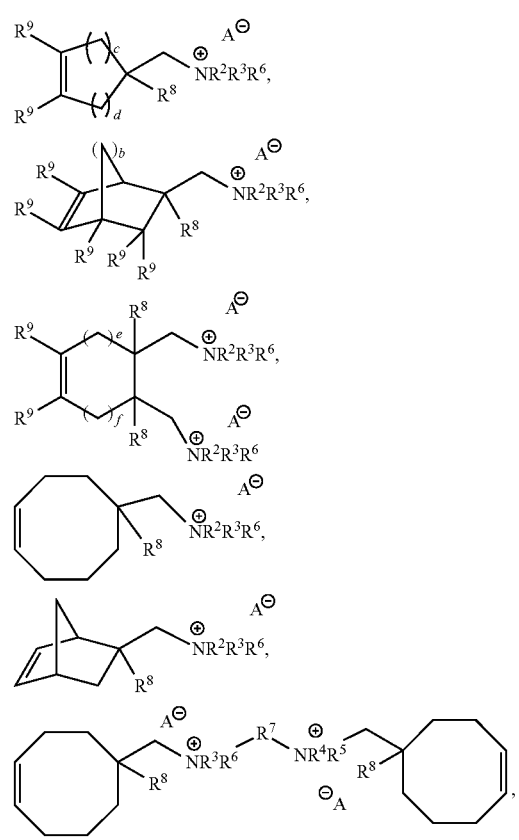

and combinations thereof. $R^2$, $R^3$, $R^4$, $R^5$, $R^6$ are, independently, a $C_1$ to $C_{20}$ group, wherein if the $C_1$ to $C_{20}$ group has a carbon in the beta position relative to the ammonium nitrogen atom then the beta carbon of the $C_1$ to $C_{20}$ group does not have a hydrogen substituent. Each $R^8$ is a $C_1$ to $C_{20}$ group. Each $R^9$ is independently selected from H and $C_1$ to $C_{20}$ group. The values of c and d are, independently, from 0 to 5. The value of b is 1 or 2. The values of e and f are, independently, from 0 to 4.

In one embodiment, the ROMP synthesis is carried out using an additional monomer selected from the following structures:

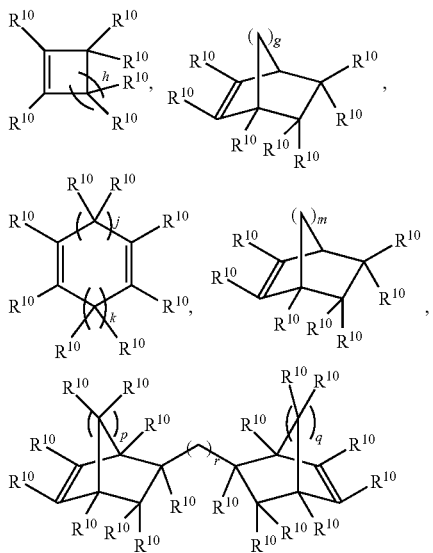

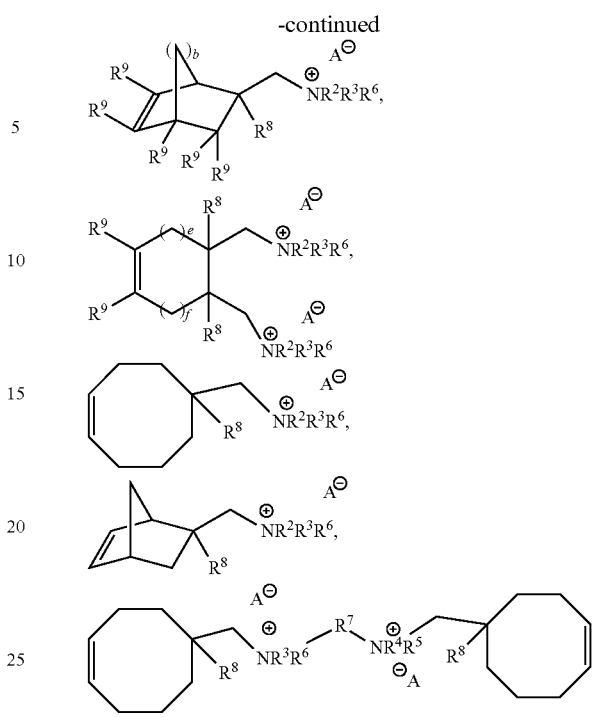

and combinations thereof. Each $R^{10}$ is independently selected from H and a $C_1$ to $C_{10}$ group. The value of h is from 1 to 10, g is 1 or 2, and j and k are, independently, from 0 to 5, except that j and k cannot both be 0 or both be 1. The value of m is 1 or 2, p and q are, independently, 1 or 2, and r is from 1 to 20.

In one aspect, the present invention provides a compound comprising at least one alkyl tetraalkylammonium group having the following structure:

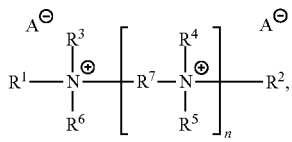

where $R^1$ is a $C_4$ to $C_{20}$ cycloalkenyl group and the carbon in the beta position relative to the ammonium nitrogen does not have a hydrogen substituent. $R^2$, $R^3$, $R^4$, $R^5$ and $R^6$ are, independently, a $C_1$ to $C_{20}$ group, and if the $C_1$ to $C_{20}$ group has a carbon in the beta position relative to the ammonium nitrogen atom then the beta carbon of the $C_1$ to $C_{20}$ group does not have a hydrogen substituent. Each $R^7$ is independently a $C_1$ to $C_{20}$ group, wherein if the $C_1$ to $C_{20}$ group has a carbon in the beta position relative to the ammonium nitrogen atom then the beta carbon of the $C_1$ to $C_{20}$ group does not have a hydrogen substituent. The counter ion, $A^-$, is selected from halide, hydroxide, hexafluorophosphate, borate, carbonate, bicarbonate and carboxylate. The value of n is from 0 to 20.

In various embodiments, the monomer is selected from the following structures:

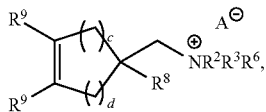

and combinations thereof. $R^2$, $R^3$, $R^6$ are, independently, a $C_1$ to $C_{20}$ group, and if the $C_1$ to $C_{20}$ group has a carbon in the beta position relative to the ammonium nitrogen atom then the beta carbon of the $C_1$ to $C_{20}$ group does not have a hydrogen substituent. Each $R^8$ is a $C_1$-$C_{20}$ group. Each $R^9$ is independently selected from H and a $C_1$ to $C_{20}$ group. The values of c and d are independently from 0 to 5. The value of b is 1 or 2. The value of e and f are, independently, from 0 to 4. Each $R^7$ is a polyatomic linking group and is comprised of a $C_1$ to $C_{20}$ group, wherein if the $C_1$ to $C_{20}$ group has a carbon in the beta position relative to the ammonium nitrogen atom then the beta carbon of the $C_1$ to $C_{20}$ group does not have a hydrogen substituent.

In another aspect, the present invention provides a hydrogen generation device, fuel cell, or water purification device comprising an ionomer of the present invention. In one embodiment, a fuel cell comprises an alkaline anion exchange membrane comprising an ionomer, where the counter ion, $A^-$, is hydroxide, and the membrane has a thickness of from 0.001 mm to 2 mm and a conductivity of at least 5 mS/cm.

BRIEF DESCRIPTION OF THE FIGURES

FIG. 14. Amounts of COE used for the different ratios and resulting conductivity values Monomer 2 (shown as 1 in figure). $^a$ Conductivity measurements were taken on two separate films with the same composition to ensure reproducibility and averaged to obtain the values used in FIG. 8. $^b$ Not applicable, did not possess sufficient mechanical integrity to warrant further study.

FIG. 15. Amounts of catalyst used for the different ratios used and the resulting conductivity values Monomer 2 (shown as 1 in figure). $^a$ Conductivity measurements were taken on two separate films with the same composition to ensure reproducibility and averaged to obtain the values used in FIG. 10. $^b$ Not applicable, did not possess sufficient mechanical integrity to warrant further study.

FIG. 16. Tensile Stress values with associated errors for the series studying the impact of COE loading (Monomer 2 shown as 1 in figure).

FIG. 17. Tensile Stress values with associated errors for the series studying the impact of catalyst loading.

FIG. 22. AAEM characterization data. $^a$ Determined by $^1$H NMR spectroscopy. $^b$ Ion exchange capacity determined by back titration, average of 3 trials. $^c$ Gravimetric water uptakes of the fully hydrated membranes, average of 5 trials. $^d$ Mechanical testing of the films in the iodide form, average of 6 trials. $^e$ Hydroxide conductivities of the AAEMs fully immersed in water at 20° C. and 50° C., average of 4 trials. $^f$ Carbonate conductivities of the AAEMs fully immersed in degassed water at 20° C. and 50° C., average of 3 trials.

FIG. 23. Solubility data for AAEM-29. $^a$ 5 wt % AAEM. +: Soluble, −: Insoluble, ±: Partially soluble.

FIG. 24. Solubility data for AAEM-33. $^a$ 5 wt % AAEM. +: Soluble, −: Insoluble, ±: Partially soluble.

DETAILED DESCRIPTION OF THE INVENTION

Figure 1:
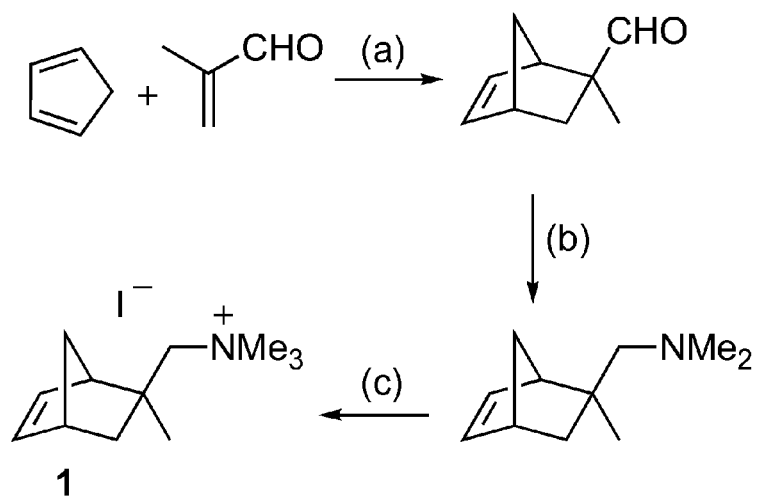
FIG. 1. Example of synthetic procedure for Monomer 1 (rac-1). (a) 10 mol % $BCl_3$, $CH_2Cl_2$, $-50°$ C., 1.5 h, 92%. (b) $Me_2NH$, $Na[BH(OAc)_3]$, 20° C., 16 h, 83%. (c) MeI, acetone, 20° C., 16 h, 80%.

The present invention provides ionomer composition with ionic moieties such as, for example, tetraalkylammonium functionalities, and methods of making the same. The present invention also provides compounds with tetraalkylammonium moieties, which can be used as monomers in the preparation of the ionomers of the present invention. The ionomers of the present invention can be used, for example, in fuel cells as alkaline anion exchange membranes.

The ionomers of the present invention contain ionic moieties, e.g., tetraalkylammonium moieties. Without intending to be bound by any particular theory, it is considered that ionomers of the present invention have continuous ionic domains, which when hydrated allow unobstructed ion conduction without the need for spatially-well defined microphase separation.

Ionomers with anchored organic cations are desirable for use as alkaline anion exchange membranes (AAEMs) because their cations cannot aggregate with anions to form a crystal lattice. Use of these materials enables operation of fuel cells under alkaline conditions in the presence of $CO_2$. Additionally, the direction of hydroxide ion conduction opposes that of methanol fuel crossover, thereby mitigating or possibly eliminating this deleterious process.

In one aspect, the present invention provides ionomers having Structure I:

Structure I where a first unit is derived from an ionic strained olefin ring monomer (an ISOM unit) and a second unit is derived from a strained olefin ring monomer which does not have an ionic moiety (a SOM unit). The ionomers are random copolymers comprising ISOM units and SOM units or ISOM units and ISOM units. In one embodiment, the ionomer comprises a predetermined number of tetraalkylammonium moieties and the tetraalkylammonium moieties are in predetermined positions.

In one embodiment, adjacent ISOM and SOM units or ISOM and ISOM or SOM and SOM units are connected by a carbon-carbon single bond or a carbon-carbon double bond. The ISOM unit is a hydrocarbon repeat unit comprising at least one alkyl tetraalkylammonium moieties. If there is a carbon atom in the beta position relative to the ammonium nitrogen then the carbon atom does not have a hydrogen substituent. The SOM unit is a hydrocarbon repeat unit. The value of x can be from 0.05 to 1, including all values to the 0.01 and ranges therebetween. The ionomer comprises a predetermined number of ionic moieties and the at least one alkyl tetraalkylammonium moiety is in a predetermined position.

The number averaged molecular weight of the ionomer, Mn, is from 5,000 to 2,000,000, including all integers and ranges therebetween. The ionomer of claim 1, wherein the weight averaged molecular weight of the ionomer, Mw, is from 5,000 to 2,000,000, including all integers and ranges therebetween. The Mn or Mw of the ionomer can be determined by routine methods such as, for example, gel permeation chromatography.

In one embodiment, the end groups of the ionomer are =CH$_2$, =CHR (where R can be CH$_2$W where W is halide, hydroxide or acetate), =CHPh, —CH$_3$, —CH$_2$R (where R can be CH$_2$W where W is halide, hydroxide or acetate) and —CH$_2$Ph.

The tetralkylammonium cations in the ionomers of the present invention can have any anion (A$^-$). Examples of suitable anions include any halide, hydroxide, hexafluorophosphate, borate, carbonate, bicarbonate and carboxylate, and the like.

In the structures below R$^1$, R$^2$, R$^3$, and R$^4$ are C$_1$ to C$_{20}$ groups. The C$_1$ to C$_{20}$ groups have from 1 to 20 carbons, including all integers therebetween, and include groups such as, for example, linear or branched alkyl groups (which can be substituted), cyclic alkyl groups (which can be saturated, unsaturated or aromatic), alkyl cyclic alkyl groups (which can be saturated, unsaturated or aromatic), and the like. Examples of C$_1$ to C$_{20}$ groups are shown in the following structures (where a wavy line indicates a point of attachment):

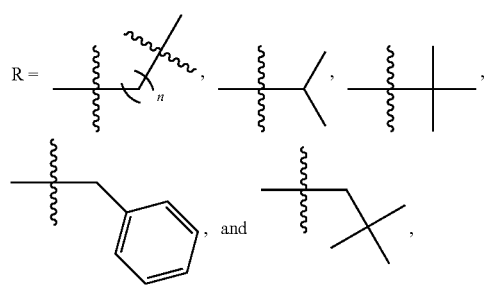

where n is from 0 to 20. For R$^1$, R$^2$, R$^3$, if the C$_1$ to C$_{20}$ group has a beta carbon relative to an ammonium nitrogen then the beta carbon of the C$_1$ to C$_{20}$ group relative to the ammonium nitrogen does not have a hydrogen substituent.

The ionomers can be crosslinked or not crosslinked. In one embodiment, the ionomers are not cross-linked. An example of an unsaturated non-crosslinked ionomer is shown in Structure II:

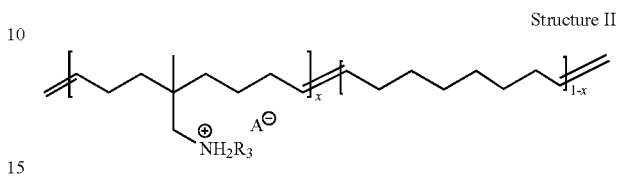

Structure II where n is from 1 to 20.

An example of a saturated non-crosslinked ionomer is shown in Structure III:

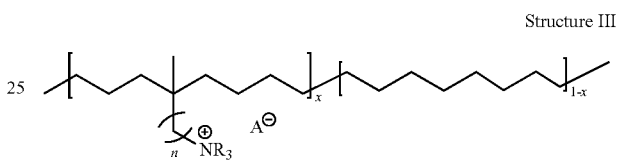

Structure III where n is from 1 to 20. For example, the values of x for ionomers of this embodiment include 0.29 or 0.33.

In another embodiment, the ionomers are crosslinked. In one embodiment, at least one first ISOM or SOM unit is connected by a polyatomic linking group (PAL) comprising a C$_1$ to C$_{20}$ group, and if the C$_1$ to C$_{20}$ group has a carbon in the beta position relative to the ammonium nitrogen atom then the beta carbon of the C$_1$ to C$_{20}$ group does not have a hydrogen substituent, to a second ISOM or SOM unit. The second ISOM or SOM unit can be in the same ionomer chain as the first ISOM or SOM unit or the second ISOM or SOM unit is a different ionomer chain than the first ISOM or SOM unit. For example, the crosslinks between the SOM units are derived from polymerization of a monomer having multiple polymerizable alkene functional groups. An example of an unsaturated SOM crosslinked ionomer is shown in the Structure IV:

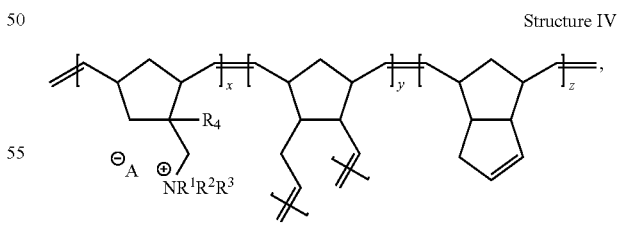

Structure IV

Where R$^4$ is a C$_1$ to C$_{20}$ group (as described above for R$^1$, R$^2$ and R$^3$). The ionomer is crosslinked by carbon-carbon double bonds between a y unit (SOM) a second y unit in the same or different ionomer chain. The value of x is from 0.05 to 1, including all values to 0.01 and ranges therebetween, and x+y+z=1. For example, the values of x for ionomers of Structure IV include 0.33 or 0.5. An example of a saturated SOM crosslinked ionomer is shown in Structure V:

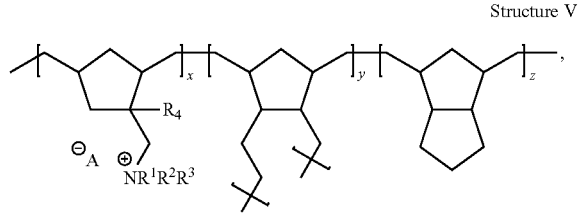

Structure V where $R^4$ is a $C_1$ to $C_{20}$ group (as described above for $R^1$, $R^2$ and $R^3$). The ionomer is crosslinked by carbon-carbon single bonds between a y unit (SOM) a second y unit in the same or different ionomer chain. The value of x is from 0.05 to 1, including all values to 0.01 and ranges therebetween, and x+y+z=1. In these two examples the SOM block is derived from dicyclopentadiene, which has multiple polymerizable alkene functional groups. For example, the values of x for ionomers of Structure V include 0.33 or 0.5

In another embodiment, the ionomers are crosslinked, where the crosslinks are derived from a multi-functional monomer having two ISOM moieties joined by a polyatomic linking group (PAL), and have, for example, Structures VI or VII:

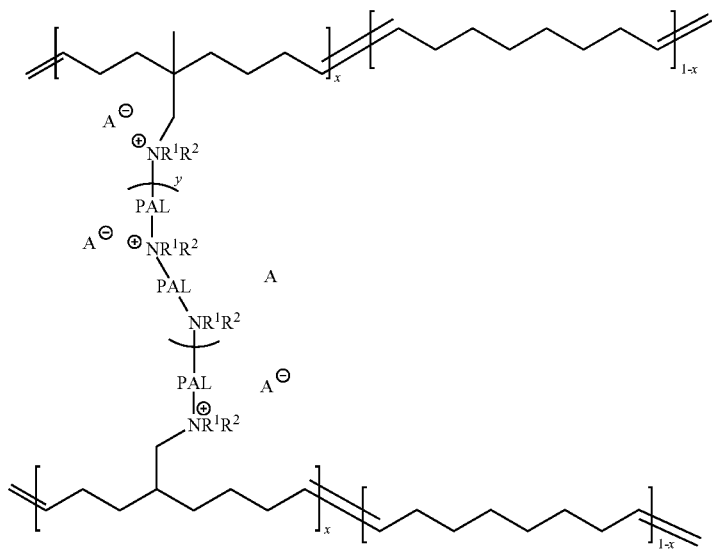

Structure VI

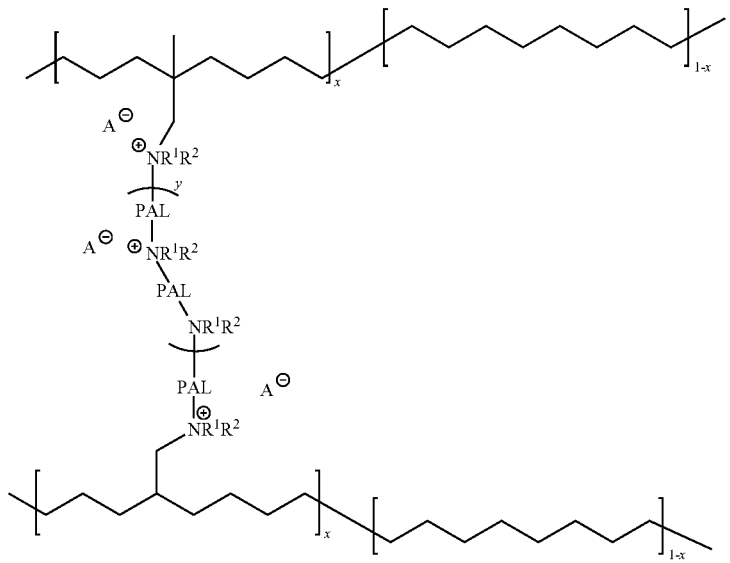

Structure VII where each PAL, independently, comprises a $C_1$ to $C_{20}$ group (as described above for $R^1$, $R^2$ and $R^3$). The value of y is from 0 to 20, including all integers and ranges therebetween. Examples of an unsaturated (Structure VIII) and saturated (Structure IX) ionomer where the crosslinks are derived from a multi-functional monomer having two ISOM moieties joined by a polyatomic linking group (PAL) is shown in the following structures:

nium nitrogen, the beta carbon does not have a hydrogen substituent. In one embodiment, $R^2$ is $C_4$ to $C_{20}$ cycloalkenyl group, such as, for example, a cyclooctene, norbornene, cyclooctadienene and the like, and the carbon in the beta position relative to the ammonium nitrogen does not have a hydrogen substituent. The value of n is from 0 to 20, including all integers and ranges therebetween. $A^-$ is any halide, hydroxide, hexafluorophosphate, any borate, any carbonate, any bicarbonate or any carboxylate.

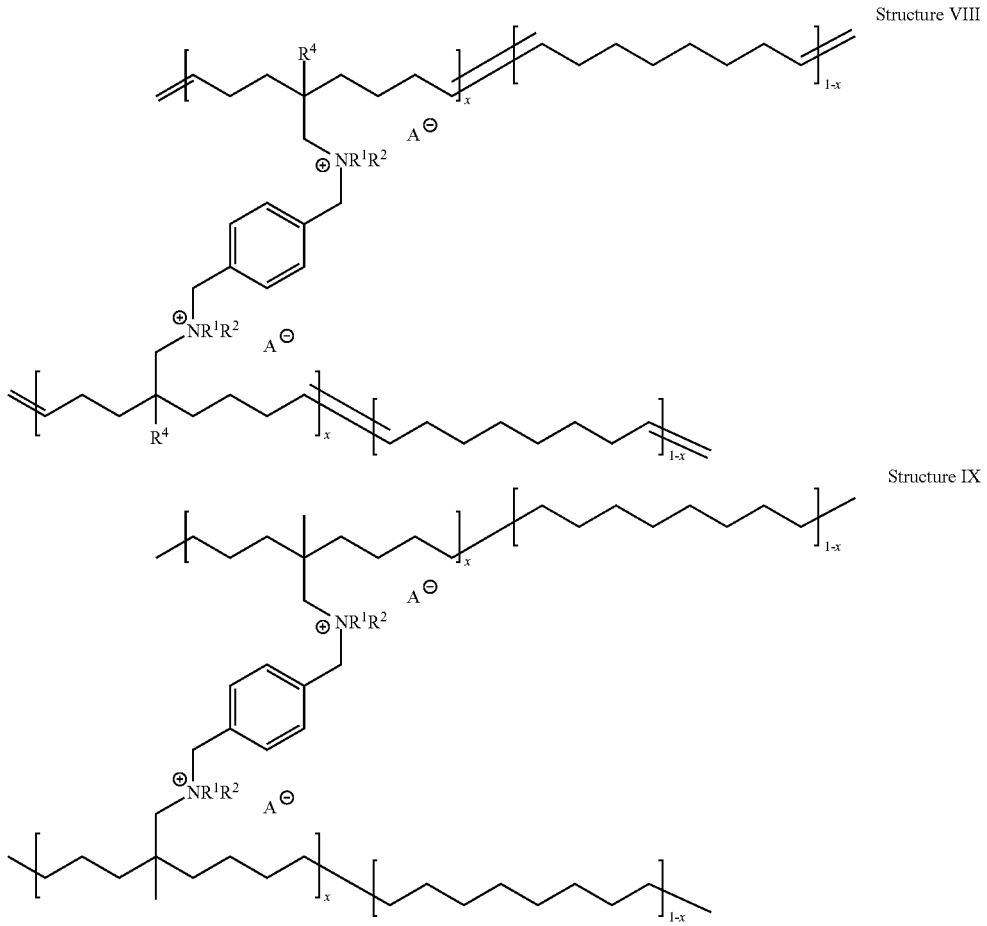

Structure VIII

Structure IX

For example, the values of x for ionomers of Structure VIII and IX include 0.25, 0.29, 0.33, 0.40 and 0.50.

In another aspect, the present invention provides compounds comprising at least one alkyl tetraalkylammonium group, which can be used as monomers from which an ISOM unit can be derived. In one embodiment, the compound has the following structure:

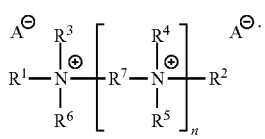

In this embodiment, $R^1$ is a $C_4$ to $C_{20}$ cycloalkenyl group, such as, for example, a cyclooctene, norbornene, cyclooctadienene, and the like. $R^2$, $R^3$, $R^4$, $R^5$, $R^6$ and $R^7$ are each, independently, a $C_1$ to $C_{20}$ group. For each of these groups having a carbon in the beta position relative to the ammo- In one embodiment, the monomer has one of the following structures:

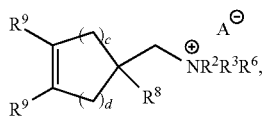

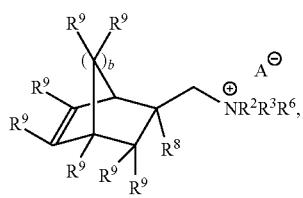

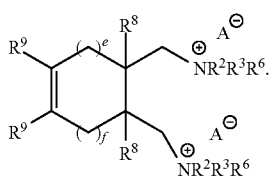

$R^2$, $R^3$, $R^6$ and $R^8$ are each, independently, a $C_1$ to $C_{20}$ group, wherein if the $C_1$ to $C_{20}$ group has a beta carbon then the beta carbon of the $C_1$ to $C_{20}$ group does not have a hydrogen substituent. Each $R^9$ is independently a H or $C_1$ to $C_{20}$ group. The values of c and d are, independently, from 0 to 5, including all integers therebetween. The value of b is 1 or 2. The values of e and f are each, independently, from 0 to 4, including all integers therebetween.

In one embodiment, the compound has one of the following structures:

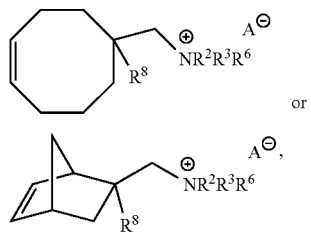

$R^2$, $R^3$, $R^6$ and $R^8$ are each, independently, a $C_1$ to $C_{20}$ group, wherein if the $C_1$ to $C_{10}$ group has a beta carbon then the beta carbon of the $C_1$ to $C_{20}$ group does not have a hydrogen substituent.

In one embodiment, the present invention provides a multifunctional monomer (MFM) which has at least two ISOM moities. These two moieties are joined by a polyatomic linking group (PAL). The MFM can have Structure X:

Structure X

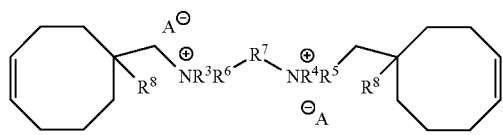

The PAL ($R^7$) is a hydrocarbon group comprising from 1 to 20 carbons, including all integers and ranges therebetween, and that connects two ammonium groups. Examples of a PAL group include groups such as, for example, linear or branched alkyl groups (which can be substituted), cyclic alkyl groups (which can be saturated, unsaturated or aromatic), alkyl cyclic alkyl groups (which can be saturated, unsaturated or aromatic), and the like. In one embodiment, $R^7$ has the following structure (where a wavy line indicates a point of attachment):

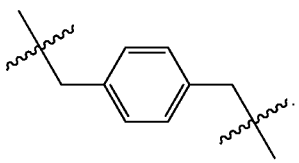 [SMILES: *Cc1ccc(C*)cc1]

In one embodiment, the MFM has the following structure:

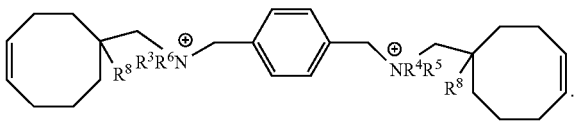

In one embodiment, the present invention provides ionomers synthesized by polymerization of the compounds described above. For example, a homopolymer of one of the compounds described above from which ISOM units are derived is produced. In another embodiment, the compounds described above and another monomer, which does not have an ionic moiety such as an alkyl tetraalkylammonium group, from which SOM unites are derived are polymerized. For example, a random copolymer of one of the compounds described above and another monomer which does not have an ionic moiety (e.g., a substituted or unsubstituted cyclooctene, norbornene or dicyclopentadiene).

The ionomers comprise ISOM units or ISOM units and SOM units. The ISOM unit is derived from a monomer (ionic strained olefin monomer—ISOM monomer), such as, for example, the compounds of the present invention described above, which has a strained ring structure and both an alkene moiety (moieties) which can be polymerized (e.g., by ring-opening metathesis polymerization) and at least one ionic moiety (e.g., a tetraalkylammonium group). The SOM unit is derived from a monomer (strained olefin monomer—SOM) which has a strained ring structure and an alkene moiety which can be polymerized (e.g., by ring-opening metathesis polymerization), but does not have an ionic moiety.

By strained ring structure it is meant that the molecule is reactive toward ring opening metathesis polymerization due to non-favorable high energy spatial orientations of its atoms, e.g., angle strain results when bond angles between some ring atoms are more acute than the optimal tetrahedral) (109.5° (for $sp^3$ bonds) and trigonal planar (120°) (for $sp^2$ bonds) bond angles.

The ionomer has ISOM units and SOM units or ISOM units and ISOM units where adjacent units are connected by a carbon-carbon single bond or a carbon-carbon double bond. For example, an ionomer having ISOM units and SOM units or ISOM units and ISOM units connected by a carbon-carbon double bond can be subjected to reaction conditions such that carbon-carbon double bonds are reduced to carbon-carbon single bonds. In one embodiment, for uncrosslinked ionomer having ISOM units and SOM units or ISOM units and ISOM units connected by carbon-carbon double bonds, 100% of the carbon-carbon double bounds are reduced to carbon-carbon single bonds. In various embodiments, for ionomers having ISOM units and SOM units or ISOM units and ISOM units connected by carbon-carbon double bonds, at least 50%, 75%, 90%, 95%, or 99% or greater than 99% or 100% of the carbon-carbon double bonds in the ionomer are reduced to carbon-carbon single bonds. Without intending to be bound by any particular theory, it is considered that hydrogenation of carbon-carbon double bonds in an ionomer increases the mechanical strength of a film made from the hydrogenated monomer.

The monomer from which a SOM unit is derived (SOM monomer) is a hydrocarbon which has at least one alkene group which can be polymerized. The SOM can have multiple alkene moieties which can result in the ionomer being crosslinked as a result of polymerization of two alkene moieties from two different SOM units. An example of such a SOM is dicyclopentadiene.

In one embodiment, the ROMP synthesis of the ionomers of the present invention is carried out using an SOM monomer selected from the following structures:

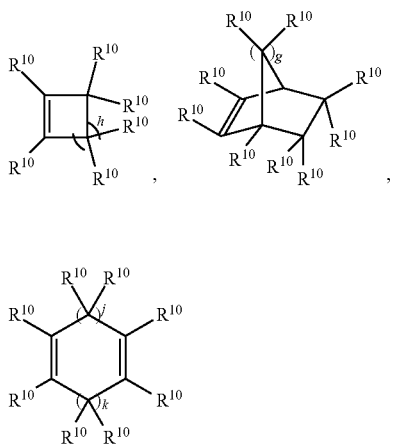

and combinations thereof. Each $R^{10}$ is independently selected from H and a $C_1$ to $C_{20}$ group (as described herein). The value of h is from 1 to 10, including all integers therebetween. The value of g is 1 or 2. The values of j and k are, independently, from 0 to 5, including all integers therebetween.

In one embodiment, the ROMP synthesis provides polymers which are crosslinked. For example, an ISOM monomer and a monomer with multiple alkene functional groups which can be polymerized such as, for example, DCPD can be copolymerized to provide crosslinked ionomers.

In one embodiment, the ROMP synthesis uses a SOM monomer having one of the following structures providing crosslinked ionomers:

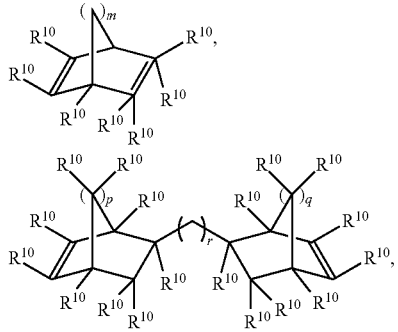

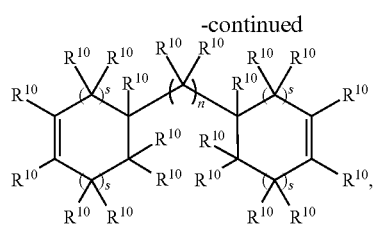

and combinations thereof. Each $R^{10}$ is independently selected from H and a $C_1$ to $C_{20}$ group (as described herein). The value of m is 1 or 2. The value of p and q are, independently, 1 or 2. The value of n is from 1 to 20, including all integers therebetween. The value of each s is, independently, from 0 to 5.

In one aspect, the present invention provides a method to synthesize ionomer materials. The ionomers can be synthesized by, for example, ring-opening metathesis polymerization (ROMP), which can be carried out using a transition metal (e.g., ruthenium-based) metathesis catalyst (e.g., a second generation Grubbs-type catalyst). The steps of the ROMP polymerization are known in the art. For example, the method includes the steps of providing an ISOM monomer and, optionally, a SOM monomer and a catalyst (such as a ruthenium-based alkene metathesis catalyst). The monomer(s) and catalyst are combined and, optionally, an appropriate solvent is added. The reaction mixture is heated under conditions such that an ionomer is formed.

In one embodiment, an ISOM monomer and a SOM monomer are combined in the presence of a catalyst (e.g., a second generation Grubbs ROMP catalyst) under conditions such that a ring-opening metathesis polymerization reaction takes place forming an ionomer having Structure I-V. The use of air-stable Grubbs'-type catalysts allows functionalized monomers to be polymerized because these catalysts are tolerant of a variety of functional groups. By employing monomers with the tetraalkylammonium moiety already present, membrane synthesis is greatly simplified because postpolymerization modifications are unnecessary.

In another embodiment, a multifunctional monomer (MFM) or a MFM and a SOM monomer are combined in the presence of a catalyst (e.g., a second generation Grubbs ROMP catalyst) under conditions such that a ring-opening metathesis polymerization reaction takes place forming, for example, an ionomer having Structure VI or VII.

It is desirable that the ionomer material have hydroxide anions. Thus, in one embodiment, if the ionomer material does not have hydroxide anions, the ionomer material is subjected to ion exchange conditions such that the non-hydroxide anions are exchanged for hydroxide anions and the resulting ionomer material has hydroxide anions.

In one aspect, the ionomer materials of the present invention can be used in devices such as, for example, fuel cells, hydrogen generators, water purification devices, and the like. In one embodiment, the present invention provides a fuel cell operating under alkaline conditions comprising an alkaline anion exchange membranes (AAEM) comprising an ionomer of Structure I.

Within a fuel cell, the ion exchange membrane serves as the conducting interface between the anode and cathode by transporting the ions while being impermeable to gaseous and liquid fuels. It is desirable that an ion exchange membrane have the four properties listed below.

An ionomer interface material is typically derived from a solvent processable ionomer. Ideally, the solvent processable ionomer should be insoluble in water and methanol or aqueous methanol, but soluble in mixtures of other low boiling point solvents (removal of a high boiling point solvent is considered difficult and unsafe in the presence of finely dispersed catalysts) such as n-propanol or aqueous n-propanol. To form the electrodes, soluble ionomer is combined with an electrocatalyst and "painted" on either a gas diffusion layer (GDL) or the membrane itself. This combination of the ionomer, electrocatalyst and GDL forms the electrode. The ionomer should also have high hydroxide conductivity.

It is desirable that the AAEM comprising the ionomer materials of the present invention have at least the following properties:

(1) low methanol solubility, and it is desirable that the ionomer be completely insoluble in methanol;

(2) hydroxide conductivity of from 1 mS/cm to 300 mS/cm, including all integers and ranges therebetween. In various embodiments, the AAEM has a hydroxide conductivity of at least 1, 5, 10, 25, 50, 100, 150, 200 or 300 mS/cm. The hydroxide conductivity is measured by methods known in the art;

(3) mechanical properties such that a membrane comprising an ionomer of the present invention does not tear or fracture under fuel cell operating conditions. In one embodiment, the membrane does not fail (e.g., tear or fracture) under a tensile stress of 1 to 500 MPa, including all integers and ranges therebetween, at a strain of 5% to 1000%, including all integers and ranges therebetween, under fuel cell operating conditions; and (4) little swelling/hydrogel formation under alkaline fuel cell conditions. In one embodiment, the swelling is from 0 to 20%, including all integers and ranges therebetween, of original AAEM film thickness. Swelling of the ion exchange membrane increases its resistance thereby decreasing its conductivity, ultimately leading to diminished fuel cell performance. If swelling results in hydrogel formation the membrane will become permeable to gases and cease to operate. As a result, excessive membrane swelling that causes hydrogel formation should be avoided.

In one embodiment, the present invention provides an AAEM comprising an ionomer of the present invention. The AAEM displays the desirable properties set out above. The thickness of the AAEM comprising the ionomer materials of the present invention can be from 1 µm to 300 µm, including all values to the 1 µm and ranges therebetween.

Water purification can be accomplished by combining, either physically or chemically, a cation exchange and anion exchange membrane into one bipolar membrane. Under the driving force of an electrical field, a bipolar membrane can efficiently dissociate water into hydrogen $H^+$ and $OH^-$ ions. The transport out of the membrane of the H+ and OH– ions obtained from the water splitting reaction is possible if the bipolar membrane is oriented correctly. The $H^+$ and $OH^-$ ions recombine producing purified water. Anion exchange membranes (AEMs) are a key component of a bipolar membrane (BPM). A BPM is a kind of composition membrane that consists of a layered ion-exchange structure composed of a cation selective layer (with negative fixed charges) and an anion selective layer (with positive fixed charges). This composition of anionic and cationic exchange layer brings about many novel applications, such as separation of mono- and divalent ions, anti-deposition, antifouling, water dissociation, and electrodialytic water splitting employing bipolar membranes to produce acids and bases from the corresponding salts. Another application of ion exchange membranes is electrochemical-ion exchange. In this process, an ion exchange membrane is bonded directly on the surface of a metal mesh electrode. By applying a current, ion exchange can be enhanced leaving, in some cases, only part per billions of metal ions in the effluent. The regeneration of the resin can be simply attained by reversing the current. This has been used for desalination of brackish water, removal of transition and main group metal ions, water softening, and nuclear waste decontamination. Electrodialysis with a bipolar membrane (BMED) can be used in the purification/separation of organic acids (for example lactic or itaconic acid) and bases from fermentation reactions.

Thus, in one embodiment, the present invention provides a water purification device comprising a bipolar membrane comprising an ionomer of the present invention. In another embodiment, the present invention provides a water electrolysis cell comprising an alkali anion exchange membrane (AAEM) comprising an ionomer of the present invention. The water electrolysis cell can be used to produce oxygen and hydrogen from water.

The following examples are presented to illustrate the present invention. They are not intended to be limiting in any manner.

Example 1

Synthesis and Characterization of ISOM Monomer and Ionomers of the Present Invention General Methods and Materials.

All reactions and manipulations of compounds were carried out in air unless otherwise specified. All solvents were used as received. Methacrolein, boron trichloride (1.0 M solution in dichloromethane), dimethylamine (2.0 M solution in tetrahydrofuran), sodium triacetoxyborohydride, potassium hydroxide flakes, and Grubbs 2nd Generation catalyst were purchased from Sigma-Aldrich and used as received. Dicyclopentadiene was also purchased from Sigma-Aldrich and was run through a plug of alumina prior to use. Methyl iodide and triethylamine were purchased from Acros Organics and Fisher Scientific, respectively, and used as received. Standardized hydrochloric acid (0.1014 N) and potassium hydroxide (0.1000±0.0001M) solutions were purchased from Sigma-Aldrich and Riedel-de Haën, respectively. Nafion 112 was purchased from Sigma-Aldrich and pretreated using a literature procedure.

Small Molecule Characterization.

$^1H$ NMR spectra were recorded on Varian INOVA 400 ($^1H$, 400 MHz) or Varian INOVA 600 ($^1H$, 600 MHz) spectrometers and referenced to $CHCl_3$, 7.26 ppm or $H_2O$, 4.80 ppm. $^{13}C$ NMR spectra were recorded on a Varian INOVA 600 ($^{13}C$, 150 MHz) spectrometer and referenced to $CHCl_3$, 77.23 ppm. The gradient selected HSQCAD, HMBCAD and ROESY spectra were recorded on a Varian Unity Inova (600 MHz) spectrometer operating at 599.757 MHz for $^1H$ observation using a Varian inverse $^1H$-{$^{13}C$, $^{15}N$} triple-resonance probehead with tripleaxis gradients. NMR data were acquired with the pulse sequences supplied in Vnmrj2.1B/Chempack 4.1 and were processed and analyzed using the MestReNova 5.3 software package (2008, Mestrelab Research S. L.). ROESY spectra were acquired using the ROESY sequence with a spectral width of 4.3 kHz. A total of 200 complex points were collected in the indirectly detected dimension with 4 scans and 0.15 acquisition time per increment. The resulting matrices were zero filled to 1k×1k complex data points and squared cosine window functions were applied in both dimensions prior to Fourier transformation. The multiplicity-edited adiabatic HSQC spectrum was acquired with the gHSQCAD sequence. Spectral widths were 4.3 kHz and 30 kHz in $^1$H and $^{13}$C dimensions, respectively. A total of 256 complex points were collected in the indirectly detected dimension with 2 scans and 0.15 s acquisition time per increment. The resulting matrices were zero filled to 2k×2k complex data points and squared cosine window functions were applied in both dimensions prior to Fourier transformation. Gradient selected adiabatic HMBC spectra were acquired in phase sensitive mode with the gHMBCAD sequence optimized for 8 Hz couplings. Spectral widths were 4.3 kHz and 36.2 kHz in $^1$H and 13C dimensions, respectively. A total of 400 complex points were collected in the indirectly detected dimension with 4 scans and 1024 points per increment. The resulting matrices were zero filled to 2k×2k complex data points and shifted sinebell window functions were applied in the $^1$H dimension prior to Fourier transformation.

Mass spectra were acquired using a JEOL GCMate II mass spectrometer operating at 3000 resolving power for high resolution measurements in positive ion mode and an electron ionization potential of 70 eV. Samples were introduced via a GC inlet using an Agilent HP 6890N GC equipped with a 30 m (0.25 μm i.d.) HP-5 ms capillary GC column. The carrier gas was helium with a flow rate of 1 mL/min. Samples were introduced into the GC using a split/splitless injector at 230° C. with a split ratio of 10:1. Elemental analysis was performed by Robertson Microlit Laboratories, Inc. Madison, N.J.

AAEM Characterization.

Ion exchange capacities (IECs) were determined using standard back titration methods. The thin film as synthesized (in iodide form) was dried under full vacuum overnight at 50° C. in order to completely dehydrate it and then weighed. Conversion to the hydroxide form was achieved by immersing the film in 3-60 mL portions of 1 M potassium hydroxide for 20 minutes each. Residual potassium hydroxide was washed away by immersing the membrane in 3-500 mL portions of deionized water for 20 minutes each. The AAEM was then stirred in 20 mL standardized 0.1 M HCl(aq) solution for 24 hours followed by titration with standardized 0.1 M KOH(aq) to determine the equivalence point. Control acid samples (with no AAEM present) were also titrated with standardized 0.1 M KOH(aq), and the difference between the volume required to titrate the control and the sample was used to calculate the amount of hydroxide ions in the membrane. This was divided by the dried mass of the membrane to give an IEC value with the units mmol OH–/g I—.

The in-plane hydroxide conductivity of the AAEM sample was measured by four probe electrochemical impedance spectroscopy (EIS) using a Solartron 1280B electrochemical workstation along with ZPlot and ZView software. The conductivity cell was purchased from BekkTech LLC (Loveland, Colo.), and a helpful schematic and description of a similar experimental setup has been reported. A strip of the thin film in iodide form (ca. 4 cm long×0.5 mm wide) was converted to the hydroxide form by immersing it in 3-30 mL portions of 1 M potassium hydroxide for 20 minutes each. Residual potassium hydroxide was washed away by immersing the membrane in 3-60 mL portions of deionized water for 20 minutes each. Aliquots of each of these water washings were removed and analyzed by inductively coupled plasma atomic emission spectrometry (ICP-AES) for potassium ions. ICP-AES was performed by the Cornell Nutrient Analysis Laboratories, Department of Crop and Soil Sciences, Cornell University using a CIROS model from Spectro Analytical Instruments, Inc. and the EPA 6010B method. Negligible potassium ions were detected in the aqueous sample (0.047 mg/L) by the third water washing; approximately equal to that detected in deionized water (0.055 mg/L) verifying complete removal of base and preventing falsely high hydroxide conductivities. The AAEM was then clamped into the cell using a Proto 6104 torque screwdriver set to 1 inch ounce and completely immersed in Millipore water (>18 MΩ·cm), at either 20° C. or 50° C., during the measurement time. In the case of the 50° C. measurement, the sample was allowed to equilibrate at that temperature for 1 hour. EIS was performed by imposing a small sinusoidal (AC signal) voltage, 10 mV, across the membrane sample at frequencies between 20,000 Hz and 0.1 Hz (scanning from high to low frequencies) and measuring the resultant current response. Using a Bode plot, the frequency region over which the impedance had a constant value was checked, and the highest frequency measurement in the Nyquist plot was taken as the effective resistance of the membrane. This was then used to calculate the hydroxide conductivity by employing the following formula: $\sigma=L/Z'\cdot A$ where L is the length between sense electrodes (0.425 cm), Z' is the real impedance response at high frequency, and A is the membrane area available for hydroxide conduction (width·thickness). The dimensional measurements were performed using a digital micrometer (±0.001 mm) purchased from Marathon Watch Company Ltd. (Richmond Hill, ON). The hydroxide conductivity was measured for four separate AAEMs (per composition) and the precision of these measurements was evaluated. All errors are determined from sample standard deviations. Confidence intervals are at the 95% confidence level based on the sample deviations and using the relevant student-t distribution (N−1 degrees of freedom, N is the number of samples tested for each membrane).

Dimensional swelling measurements were carried out in either deionized water (10 mL) or 2 M aqueous methanol solution (0.81 mL methanol in 10 mL deionized water) pre-heated to 60° C. Two stamp-sized pieces were cut out of an AAEM sample and their length, width and thickness measurements were recorded followed by placement of the samples in either one of the above solutions for 2 hours. At this time, the measurements were repeated and the dimensional swelling expressed as the percent difference between the two volumes.

The mechanical properties of the thin films in the iodide form were characterized using an Instron system (model 5566) (Instron Co., Canton, Mass.) using a 100 N static lodge cell and Blue Hill software. The tensile strength of two strips from each of two wet samples were measured in the iodide form (i.e., four measurements total).

Preparation of 2-methylbicyclo[2.2.1]hept-5-ene-2-carbaldehyde. To a solution of freshly cracked cyclopentadiene (14.0 mL, 172 mmol) in 125 mL dichloromethane at −50° C., methacrolein (18.5 mL, 224 mmol) and boron trichloride solution (17.0 mL, 17.0 mmol) were added sequentially under nitrogen. After these additions, stirring was commenced and the reaction allowed to proceed at −50° C. for 90 minutes. Triethylamine (10.0 mL, 71.7 mmol) was then added via syringe and the reaction allowed to warm to room temperature. 125 mL of water were then added resulting in a biphasic yellow mixture, which was separated. The aqueous fraction was then extracted with 2×100 mL portions of dichloromethane, combined with the separated organic fraction and dried with magnesium sulfate. The clear, yellow solution was then dried by rotary evaporation affording 2-methylbicyclo[2.2.1]hept-5-ene-2-carbaldehyde (21.7 g, 159 mmol), as 85% exo aldehyde diastereomer, in 92% yield as an orange liquid which partially solidified upon standing at room temperature. The compound was generally used as is, but further purification could be carried out by distilling under full vacuum at 65° C. resulting in the isolation of the pure aldehyde as a colorless liquid/solid.

The NMR shifts closely match those in the aforementioned literature procedure for the exo isomer. $^1$H NMR (400 MHz, CDCl3) δ 9.65 (1H, CHO), 6.25 (1H, dd, 3J=5.6 Hz, CHO 3.2 Hz, CH=CH), 6.06 (1H, dd, 3J=5.6 Hz, 2.8 Hz, CH=CH), 2.85 (1H, b, Bridgehead CH), 2.77 (1H, b, Bridgehead CH), 2.20 (1H, dd, 2J=12 Hz, 3J=4.0 Hz, CH2), 1.35 (1H, m, Bridge CH), 1.25 (1H, m, Bridge CH), 0.96 (3H, s, CH3), 0.72 (1H, d, 2J=12 Hz, CH2). $^{13}$C NMR (150 MHz, CDCl3) δ 205.9, 139.7, 133.2, 54.0, 50.9, 48.6, 43.4, 34.8, 20.2.

Preparation of N,N-dimethyl-1-(2-methylbicyclo[2.2.1]hept-5-en-2-yl)methanamine. To a solution of 2-methylbicyclo[2.2.1]hept-5-ene-2-carbaldehyde (14.3 g, 105 mmol) in 150 mL of tetrahydrofuran, dimethylamine solution (68.0 mL, 136 mmol) was added and stirred at 20° C. for 2 hours. At this time, Na[BH(OAc)3] (28.9 g, 136 mmol) was slowly added, diluted with a further 100 mL of tetrahydrofuran to loosen the slurry and stirred overnight. The reductant was quenched with 1 M aqueous potassium hydroxide (150 mL, 150 mmol) causing the reaction mixture to turn clear yellow. After 15 minutes, the solution was extracted with 3×100 mL portions of diethyl ether and dried with magnesium sulfate. The clear, yellow solution was then dried by rotary evaporation affording N,N-dimethyl-1-(2-methylbicyclo[2.2.1]hept-5-en-2-yl)methanamine (14.4 g, 87.1 mmol) in 83% yield as a yellow-orange liquid. The compound was generally used as is, but further purification could be carried out by distilling under full vacuum at 50° C. resulting in the isolation of the pure amine as a colorless liquid. The resonances for the exo and endo isomers (ca. 4:1, respectively) were assigned with the aid of gHMBC, gHSQC, and ROESY experiments. For the exo-isomer: 1H NMR (600 MHz, CDCl3) δ 6.07 (1H, dd, 3J=5.7 Hz, 2.9 NMe2 Hz, CH=CH), 6.04 (1H, dd, 3J=5.7 Hz, 3.1 Hz, CH=CH), 2.71 (1H, m, Bridgehead CH), 2.47 (1H, m, Bridgehead CH), 2.39 (1H, d, 2J=13.2 Hz, CH2N(CH3)2), 2.28 (1H, d, 2J=13.2 Hz, CH2NMe2), 2.26 (6H, s, N(CH3)2), 1.55 (1H, ddd, 2J=8.4 Hz, 3J=1.5 Hz, 3J=1.5 Hz, Bridge CH), 1.49 (1H, dd, 2J=11.5 Hz, 3J=3.8 Hz, CH2), 1.30 (1H, ddd, 2J=8.4 Hz, 3J=2.7 Hz, 3J=1.8 Hz, Bridge CH), 0.89 (3H, s, CH3), 0.78 (1H, dd, 2J=11.5 Hz, 3J=2.6 Hz, CH2). 13C NMR (150 MHz, CDCl3) δ 136.9, 136.0, 71.6, 50.6, 48.4, 47.7, 43.5, 42.8, 39.7, 24.6. For the endo-isomer: $^1$H NMR (600 MHz, CDCl3) δ 6.09 (1H, dd, 3J=5.6 Hz, 2.9 Hz, CH=CH), 6.05 (1H, m, CH=CH), 2.69 (1H, m, Bridgehead CH), 2.43 (1H, m, Bridgehead CH), 2.18 (6H, s, N(CH3)2), 2.13 (1H, d, 2J=12.8 Hz, CH2N(CH3)2), 1.91 (1H, d, 2J=12.8 Hz, CH2NMe2), 1.58 (1H, ddd, 2J=8.4 Hz, 3J=1.5 Hz, 3J=1.5 Hz, Bridge CH), 1.41 (1H, dd, 2J=11.5 Hz, 3J=3.8 Hz, CH2), 1.32 (1H, m, Bridge CH), 1.21 (3H, s, CH3), 0.86 (1H, dd, 2J=11.5 Hz, 3J=2.6 Hz, CH2). $^{13}$C NMR (150 MHz, CDCl3) δ 136.3, 135.5, 69.7, 52.4, 47.8, 47.5, 42.9, 42.1, 40.6, 26.3. HRMS EI (m/z): calc. for C11H19N, 165.1517. found, 165.1522.

Preparation of N,N,N-trimethyl-1-(2-methylbicyclo[2.2.1]hept-5-en-2-yl)methanaminium iodide (Monomer 1): To a solution of N,N-dimethyl-1-(2-methylbicyclo[2.2.1]hept-5-en-2-yl)methanamine (12.5 g, 75.6 mmol) in 125 mL acetone, methyl iodide (7.1 mL, 114 mmol) was added dropwise and stirred at 20° C. with the formation of a white precipitate occurring after 2 minutes. After stirring for 16 hours to ensure complete reaction, 100 mL n-pentane was added to the reaction mixture and filtered. The white powder was washed with 3-100 mL portions of n-pentane, isolated and dried under vacuum affording 1 (18.5 g, 60.2 mmol) in 80% yield. Monomer 1 can be recrystallized from hot dichloromethane, chloroform, or acetonitrile, at 4° C. yielding single crystals as the exo isomer exclusively. $^1$H NMR (600 MHz, CDCl3) δ 6.19 (1H, dd, 3J=6.0 Hz, 3.0 Hz, CH=CH), 6.05 (1H, dd, 3J=6.0 Hz, 3.0 Hz, CH=CH), 3.88 (2H, m, CH2N(CH3)2), 3.55 (9H, s, N(CH3)3), 2.90 (1H, b, Bridgehead CH), 2.67 (1H, b, Bridgehead CH), 2.09 (1H, dd, 2J=12.0 Hz, 3J=4.2 Hz, CH2), 1.85 (1H, d, 2J=9.0 Hz, Bridge CH), 1.43 (1H, d, 2J=9.0 Hz, Bridge CH), 1.17 (3H, s, CH3), 0.96 (1H, dd, 2J=12.0 Hz, 3J=3.0 Hz, CH2). $^{13}$C NMR (150 MHz, CDCl$_3$) δ 138.2, 134.8, 77.6, 56.2, 52.4, 48.4, 44.4, 43.3, 40.4, 25.8. Anal. calc. for C12H22NI: C, 46.92; H, 7.22; N, 4.56. Anal. found: C, 47.18; H, 7.33; N, 4.55.

Control Measurements of Nafion 112. The average proton conductivity values measured for four samples at 20° C. and 50° C. were 75±2 mS/cm and 112±3 mS/cm, respectively. The average tensile stress and strain at maximum loads measured for two samples were 31.5 MPa at 194%. The percent dimensional swelling measurements of two stamp-sized samples in 60° C. deionized water and 2 M aqueous methanol were 1.0% and 2.2%, respectively.

Preparation of AAEM with 2:1 Molar Ratio of Dicyclopentadiene. Monomer 1. To a solution of Monomer 1 (0.053 g, 0.17 mmol) and dicyclopentadiene (0.046 g, 0.35 mmol) in 2.0 mL chloroform, a solution of Grubbs' 2nd Generation catalyst (0.0030 g, 0.0035 mmol) in 0.6 mL chloroform was added and stirred for 1 minute at 20° C. At this time, the orange reaction mixture was deposited onto a flat glass Petri dish sitting on a hot plate pre-heated to a surface temperature of ca. 30° C. with a thin metal plate separating the two in order to ensure uniform heating. Within a fumehood, a round glass cover with a volume of 550 mL and a diameter of 7 cm and a Kontes valve affixed at the top to control the rate of solvent evaporation was placed over the Petri dish to prevent drafts yielding even films. The reaction mixture solidified after 120-150 minutes, at which time the cover was removed and the surface temperature increased to ca. 75° C. for 1 hour to ensure all volatiles were removed. The sample was then cooled, and deionized water added to the Petri dish in order to ease removal of the film. The measured IEC for two separate AAEMs was 0.96 and 1.04 mmol OH−/g giving an average value of 1.0 mmol OH−/g. The average hydroxide conductivity values measured for four separate AAEMs at 20° C. and 50° C. were 14±2 mS/cm and 21±4 mS/cm, respectively.

The percent dimensional swelling measurements were:

| | |
|---|---|
| Sample 1 (2M methanol): 2.2% | Sample 1 (deionized water): 0% |
| Sample 2 (2M methanol): 1.1% | Sample 2 (deionized water): 1.1% |
| Average: 1.7% (methanol) | 0.55% (deionized water) |

A single dimensional swelling experiment employing four stamp-sized pieces from the same AAEM sample was also performed as a means of determining the maximum concentration of aqueous methanol the membrane could tolerate (e.g. percent swelling less than 10%) at 60° C. The four pieces, in the hydroxide form, were measured as above and immersed in pre-heated solutions of 4 M, 6 M, 8M and 10 M aqueous methanol. After two hours, the samples' dimensions were re-measured giving percent swelling values of 3.7%, 3.7%, 5.4% and 20.7%, respectively. The average tensile stress and strain at break measurements for four thin films were 16±6 MPa and 7.2±3%, respectively.

Preparation of AAEM with 1:1 Molar Ratio of Dicyclopentadiene. Monomer 1. To a solution of Monomer 1 (0.070 g, 0.23 mmol) and dicyclopentadiene (0.030 g, 0.23 mmol) in 2.0 mL chloroform, a solution of Grubbs' 2nd Generation catalyst (0.0019 g, 0.0022 mmol) in 0.3 mL chloroform was added and stirred for 1 minute at 20° C. At this time, the orange reaction mixture was deposited onto a flat glass dish, and the AAEM generated as above. The measured IEC for two separate AAEMs was 1.39 and 1.31 mmol OH–/g giving an average value of 1.35 mmol OH–/g. The average hydroxide conductivity values measured for four separate AAEMs at 20° C. and 50° C. were 18.2±2.1 mS/cm and 27.9±3.4 mS/cm, respectively.

The average tensile stress and strain at break measurements for four thin films were 2.3±0.5 MPa and 26±3%, respectively.

Single-Crystal X-Ray Crystallography.

Crystals of Monomer 1 were transferred from a crystallization vessel onto a microscope slide in a drop of viscous organic oil. Using a nylon loop, a suitable single crystal was chosen and mounted on a Bruker X8 APEX II diffractometer (MoKα radiation) and cooled to 0° C. Data collection and reduction were done using Bruker APEX24 and SAINT+5 software packages. An empirical absorption correction was applied with SADABS. Structure was solved by direct methods and refined on F2 by full matrix least-squares techniques using SHELXTL7 software package. All non-hydrogen atoms were refined anisotropically. Hydrogen atoms were added to the model in their geometrically ideal positions. Colorless plate like crystals belong to a monoclinic P2(1)/c space group. The sample size was 0.30×0.20× 0.05 mm3. Overall 16041 reflections were collected, 4203 of which were unique (Rint=0.0264); with 3393 'strong' reflections (Fo>4σFo). Final R1=3.22%. Crystallographic data (excluding structure factors) have been deposited with the Cambridge Crystallographic Data Center. Copies of the data can be obtained free of charge on application to CCDC, 12 Union Road, Cambridge CB2 1EZ, UK (fax: (+44)1223-336-033; email: deposit@ccdc.cam.ac.uk).

A ROMP route was used to prepare examples of ionomers of the present invention, as olefin metathesis is an extraordinarily powerful C—C bond forming reaction, and the use of air-stable Grubbs' 2nd Generation catalyst ([Ru]) enables functionalized monomers to be polymerized due to its exceptional tolerance. By employing monomers with the tetraalkylammonium moiety already present, AAEM synthesis is greatly simplified because post-polymerization modifications are unnecessary. Monomer 1 was prepared in three straightforward steps in 62% overall isolated yield as a crystalline solid (FIG. 1). The lack of beta-hydrogen atoms in Monomer 1 prevents degradation by Hofmann elimination and increases ammonium group stability. Additionally, trimethylammonium groups exhibit good stability under alkaline conditions at elevated temperatures.

Figure 2:
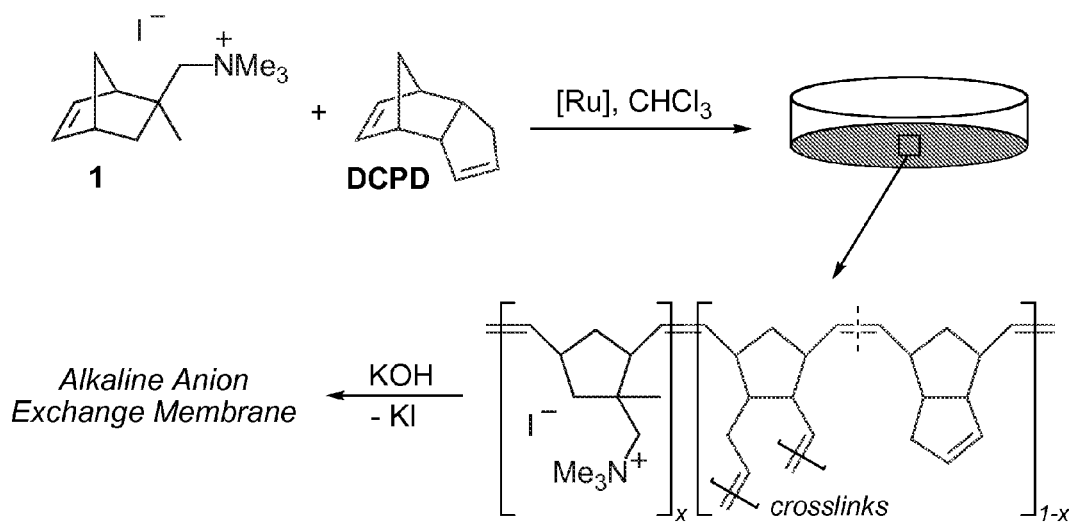
FIG. 2. Example of synthesis/preparation of AAEM.

In the present work, thin copolymer films were synthesized by combining [Ru] with a chloroform solution of Monomer 1 and DCPD at room temperature (FIG. 2). After one minute of vigorous stirring, the homogeneous solution was transferred to a flat, pre-heated glass dish where the polymerization continued, followed by solvent evaporation yielding the clear, thin film.

The thickness and properties of the films could be easily controlled by simply varying the amount and molar ratios, respectively, of 1 to DCPD. Upon conversion to the hydroxide form, it became clear that films with Monomer 1 as the major component (e.g. a molar ratio of Monomer 1:DCPD greater than 1:1) could not be quantitatively evaluated due to significant swelling and hydrogel formation. Similarly, AAEMs comprised of considerable amounts of DCPD (e.g. a ratio of DCPD:1 greater than 2:1) were exceptionally strong, but were not sufficiently conductive due to decreased ionicity.

Figures 3, 4, 5:
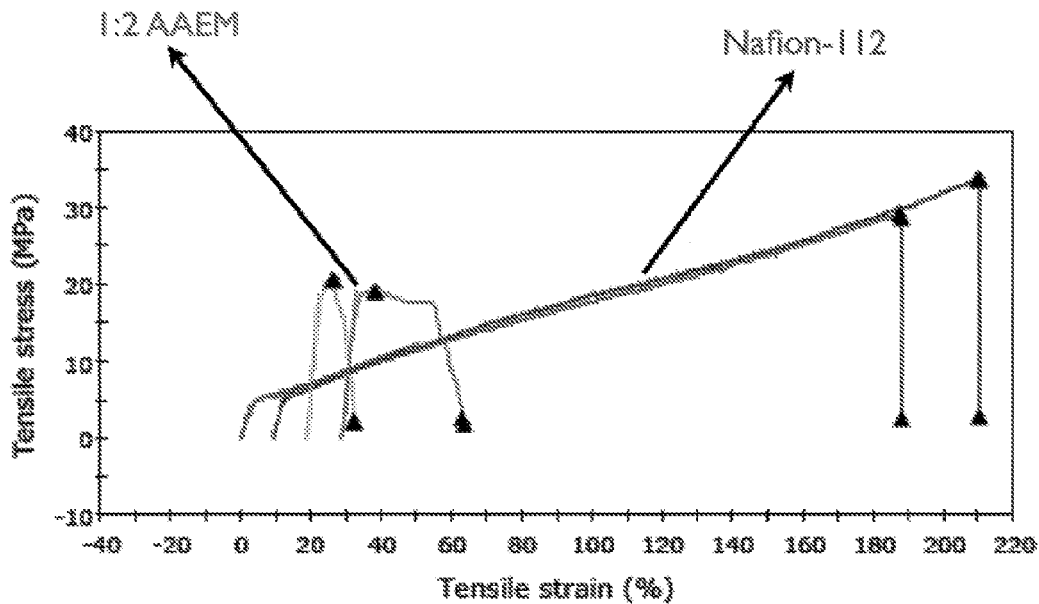
FIG. 3. Characterization data for examples of AAEMs synthesized by the ROMP of Monomer 1 (shown as 1 in figure) and dicylopentadiene (DCPD). [a] Ion exchange capacity determined by titration, average of 2 trials. [b] Three-dimensional swelling of AAEM after sitting in 2 M aqueous methanol at 60° C. for 2 hours, average of 2 trials. [c] Not determined due to uncontrollable curling of the film. [d] Mechanical testing of the films, average of 4 trials. [e] Hydroxide conductivities of the AAEMs fully immersed in water, average of 4 trials. $\sigma_{20}$ and $\sigma_{50}$ are measurements at 20° C. and 50° C., respectively.
FIG. 4. Conductivity data for DPCD copolymers with Monomer 1 (shown as M in figure).
FIG. 5. Mechanical testing data for 1:2 DPCD copolymers with Monomer 1.

Overall, our studies indicated that desirable AAEMs, with respect to mechanical integrity and hydroxide conductivity, had a DCPD: Monomer 1 molar ratio of either 2:1 or 1:1. Detailed characterization data are provided in FIG. 3. The average ion exchange capacities (IECs) for the 2:1 and 1:1 samples are 1.0 and 1.4 mmol OH–/g, respectively, and fall into the range observed for Nafion-115 (0.92 mmol $H^+$/g)14 as well as AAEMs reported by other groups. The theoretical IECs for the 2:1 and 1:1 films are 1.75 and 2.28 mmol OH–/g, respectively; such variations are commonly observed. We also evaluated the dimensional swelling of the 2:1 sample. An ideal membrane will not swell appreciably in length, width, or thickness upon exposure to solvents contained within a fuel cell at typical operating temperatures (50-80° C.). Encouragingly, our results indicate that negligible swelling occurs in 2 M aqueous methanol after two hours at 60° C. To further test the methanol tolerance of this material, we performed the same measurements using more concentrated aqueous methanol solutions. Indeed significant swelling (e.g. >10%) was not observed until immersion into methanol solutions greater than 8 M. This exceptional methanol tolerance is likely attributable to the presence of the hydrocarbon DCPD crosslinker as the major component.

The mechanical properties of both samples were evaluated using tensile stress-strain measurements. The 2:1 sample exhibited considerable tensile strength with an average 15.8 MPa of stress resulting in 7.2% strain. The toughness of the 2:1 film can also be accounted for by the crosslinked DCPD regions. Further supporting this is the dramatic decrease in toughness observed with lower DCPD loadings; only 2.3 MPa were required to break the 1:1 sample.

The in-plane hydroxide conductivity was determined for each film composition at both 20° C. and 50° C. The 2:1 sample had a conductivity of 14 mS/cm at room temperature that increased to 21 mS/cm at 50° C. Moreover, increasing the ionicity with higher loadings of 1 in the 1:1 sample led to higher conductivities. At 20° C., this membrane exhibited conductivity at 18 mS/cm that rose to 28 mS/cm at 50° C. This places the 1:1 film among the highest conducting AAEMs reported to date.

In summary, we have developed a ROMP route to AAEMs via the copolymerization of Monomer 1 with DCPD. The thin films generated are mechanically strong, exhibit desirable hydroxide ion conductivities and methanol tolerance.

Example 2

Synthesis and Characterization of ISOM Monomer and Ionomers of the Present Invention This example describes synthetic approaches to AAEMs in which the entire material contains tetraalkylammonium functionalities leading to continuous ionic domains, thereby allowing unobstructed ionic conduction without the need for microphase separation. Materials with such high ionic content can suffer from significant swelling unless crosslinks between polymer chains are installed to minimize this undesirable effect. Additionally, we sought to develop a system that does not require post polymerization modifications to attach tetraalkylammonium functionalities because crosslinking can hinder such reactions. Introduction of tetraalkylammonium groups to the monomer prior to the polymerization process provides a more straightforward AAEM synthesis.

General Methods and Materials.

All errors are determined from sample standard deviations. Confidence intervals are at the 95% confidence level based on the sample deviations and using the relevant student-tdistribution (N−1 degrees of freedom, N is the number of samples tested for each membrane composition).

All reactions and manipulations of compounds were carried out in air unless otherwise specified. Dimethylamine (2.0 M solution in tetrahydrofuran), sodium triacetoxyborohydride, potassium hydroxide, potassium bicarbonate, potassium carbonate, tert-butyl alcohol, oxalyl chloride (98%), triethylamine, $\alpha,\alpha'$-dibromo-p-xylene, cis-cyclooctene (95%), Grubbs' $2^{nd}$ Generation catalyst, standardized hydrochloric acid (0.1014 M) and standardized potassium hydroxide (0.1000±0.0001 M) were purchased from Sigma-Aldrich and used as received. Cyclooctadiene (99%), butyllithium (1.6 M solution in hexanes), methyl iodide (99%), and lithium aluminum hydride (4.0 M solution in diethyl ether) were all purchased from Acros Organics and used as received. Diisopropylamine was purchased from Sigma-Aldrich and vacuum transferred from calcium hydride. All solvents were purchased from Sigma-Aldrich or Mallinckrodt. Tetrahydrofuran and diethyl ether were dried by passage over an alumina packed drying column. Carbon monoxide (99.99%) was purchased from Matheson gases. Palladium (II) chloride and calcium hydride was purchased from Strem Chemicals. Nafion 112 was purchased from Sigma-Aldrich and pretreated using a literature procedure.

Small Molecule Characterization.

$^1$H and $^{13}$C NMR spectra were recorded on a Varian MERCURY 300 ($^1$H, 300 MHz, $^{13}$C, 75 MHz) and referenced to benzene, 7.16/128.39 ppm. The gradient selected HMBCAD spectrum was recorded on a Varian Unity INOVA (600 MHz) spectrometer operating at 599.757 MHz for $^1$H observation using a Varian inverse $^1$H-[$^{13}$C, $^{15}$N] triple-resonance probehead with triple-axis gradients. The sample was dissolved in a 1:1 mixture CD3OD:CDCl3 (referenced to chloroform at 7.27/77.23 ppm). NMR data were acquired with the pulse sequences supplied in Vnmrj 2.1B/Chempack 4.1 and were processed and analyzed using the MestReNova 5.3 software package (2008, Mestrelab Research S. L.). Gradient selected adiabatic HMBC spectra were acquired in phase sensitive mode with the gHMBCAD sequence optimized for 8 Hz couplings and the low pass filter disabled to retain one-bond correlations. Spectral widths were 4.5 kHz and 36.2 kHz in $^1$H and $^{13}$C dimensions, respectively. A total of 400 complex points were collected in the indirectly detected dimension with 2 scans and 1024 points per increment. The resulting matrices were zero filled to 2k×2k complex data points and shifted sinebell window functions were applied in the 1H dimension prior to Fourier transformation. Mass spectra were acquired using a JEOL GCMate II mass spectrometer operating at 3000 resolving power for high resolution measurements in positive ion mode and an electron ionization potential of 70 eV. Samples were introduced via a GC inlet using an Agilent HP 6890N GC equipped with a 30 m (0.25 μm i.d.) HP-5 ms capillary GC column. The carrier gas was helium with a flow rate of 1 mL/min. Samples were introduced into the GC using a split/splitless injector at 230° C. with a split ratio of 10:1. Elemental analysis was performed by Robertson Microlit Laboratories, Inc. Madison, N.J.

Ion Exchange Procedure.

Films were soaked in deionized water for at least 24 hours prior to hydroxide ion exchange. Hydroxide ion exchange for bromide ions is accomplished by using three consecutive washes with 1 M potassium hydroxide (150 mL) for 20 minutes each followed by three consecutive washes with deionized water (150 mL) for 20 minutes each. This procedure is used in all cases where films are converted to the hydroxide form. We verified this procedure was sufficient for removing all residual potassium hydroxide from our materials by analyzing the washing solutions for potassium ions with inductively coupled plasma atomic emission spectrometry (ICP-AES). The washing solutions following the first wash were all negative for potassium, including the solution in which the AAEM was soaked for 24 hours following the ion exchange procedure. This ensured that our conductivity measurements were the result of tetraalkylammonium hydroxide ions only since no residual potassium hydroxide was embedded in the material. Additionally, elemental analysis of our AAEMs for bromide was negative following the ion exchange and washing process, indicating that the ion exchange is complete. ICP-AES was performed on the aqueous washing samples by the Cornell Nutrient Analysis Laboratories, Department of Crop and Soil Sciences, Cornell University using a CIROS model from Spectro Analytical Instruments, Inc. and the EPA 6010B method. 1 M solutions of potassium chloride, carbonate or bicarbonate were used in place of potassium hydroxide to obtain the films with the counterions listed in FIG. 9. All other variables remained the same during the ion exchange for these materials. Ion Conductivity.

The in-plane hydroxide conductivity of the AAEM sample was measured by four probe electrochemical impedance spectroscopy (EIS) using a Solartron 1280B electrochemical workstation along with ZPlot and ZView software. The conductivity cell was purchased from BekkTech LLC (Loveland, Colo.), and a helpful schematic and description of a similar experimental setup has been reported. Samples to be tested (ca. 4 cm×0.5 mm) were subjected to ion exchange as described above, then clamped into the cell using a Proto 6104 torque screwdriver set to 1 inch ounce. This assembly was completely immersed in Millipore water (>18 MΩ·cm) pre-equilibrated to the desired temperature and then immediately measured. This was done to eliminate any potential interference caused by reaction of the hydroxide ions with dissolved carbon dioxide. EIS was performed by imposing a small sinusoidal (AC signal) voltage, 10 mV, across the membrane sample at frequencies between 20,000 Hz and 0.1 Hz (scanning from high to low frequencies) and measuring the resultant current response. Using a Bode plot, the frequency region over which the impedance had a constant value was confirmed, and the real impedance value at the highest frequency measurement in the Nyquist plot was taken as the effective resistance of the membrane. This was then used to calculate the hydroxide conductivity by employing the following formula: $\sigma = L/Z' \cdot A$ where L is the length between sense electrodes (0.425 cm), Z' is the real impedance response at high frequency, and A is the membrane area available for hydroxide conduction (width·thickness). The dimensional measurements were performed using a digital micrometer (±0.001 mm) purchased from Marathon Watch Company Ltd. (Richmond Hill, ON, Canada).

Ion Exchange Capacity.

Ion exchange capacities (IECs) were determined using standard back titration methods. The AAEM was prepared as previously stated and then immediately immersed into 30 mL standardized 0.1 M HCl(aq) solution for 48 hours with gentle stirring followed by titration to the equivalence point with standardized 0.1 M KOH(aq). Control acid samples (with no AAEMs present) were also titrated with standardized 0.1 M KOH(aq), and the difference between the volume required to titrate the control and the sample was used to calculate the content of hydroxide ions in the membrane. The sample was then dried under vacuum at 50° C. for at least 12 hours to obtain the dried mass of the material in the chloride form. The moles of hydroxide in the sample was divided by the dried mass of the membrane to give an IEC value with the units mmol OH–/g material in the Cl– form.

Dimensional Change and Water Uptake.

Dimensional swelling measurements were carried out in aqueous methanol solutions (8, 10 and 12 M solutions pre-heated to 60° C.). Six small pieces (c.a. 0.5 cm×0.5 cm×80 μm) were cut from a film in the bromide form. These were converted to the hydroxide form using the procedure described above (except using 30 mL of 1 M KOH due to smaller sample size) and their length, width and thickness measurements were recorded immediately after the hydroxide exchange process followed by placement of the samples in one of the above solutions for 2 hours. At this time, the measurements were repeated and the dimensional swelling expressed as the percent difference between the two volumes.

Water uptake was determined from the mass difference between the fully hydrated and dried AAEMs. Immediately following hydroxide ion exchange, a sample was dried with a paper towel and placed in a capped vial to ensure accurate weighing. The sample was then dried at 50° C. under vacuum for 12 hours and then re-weighed. The water uptake percentage value was calculated by: $WU=[(Mass_{final}-Mass_{initial})/Mass_{initial}]*100$.

Mechanical Property Analysis.

The mechanical properties of the film samples in the bromide form were characterized using an Instron system (Model 5566) (Instron Co., Canton, Mass.) equipped with a 100 N static Lodge cell and Blue Hill software. Measurements were taken on samples immediately removed from water after being soaked for at least 24 hours to ensure complete hydration.

Transmission Electron Microscopy.

For TEM analysis, a piece of the sample optimized for conductivity (Br— form) was embedded in Quetol 651 embedding media and polymerized at 60° C. for two hours. The samples were then ultramicrotomed on a Reichert Ultracut to a thickness of ~60 nm and picked up on a 200 mesh copper TEM grid. Images were taken on an FEI Tecnai 12S/TEM at 120 kV.

Differential Scanning Calorimetry.

DSC analyses were performed (Br— form) using a Mettler DSC1/700 using the STARe software package Version 9.10. The method used was 10° C./min ramp, with one cycle of heat, cool, and heat again with a temperature range of −40 to 100° C.

Monomer Synthesis.

Figure 11:
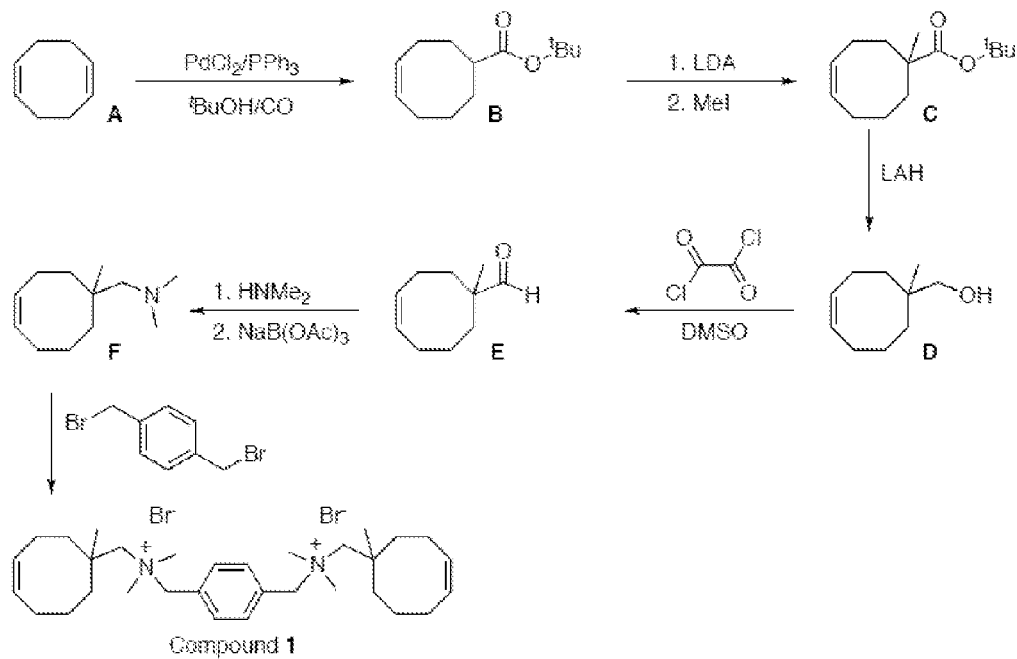
FIG. 11. Example of general scheme for synthesis of Monomer 2 (shown as Compound 1 in figure).
Figure 12:
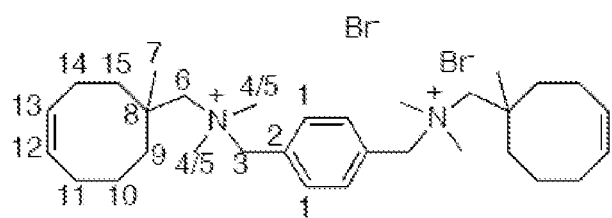
FIG. 12. $^1$H and $^{13}$C NMR Assignments for Monomer 2 (shown as 1 in figure) (gHMBC spectrum shown in FIG. 13)
Figure 13:
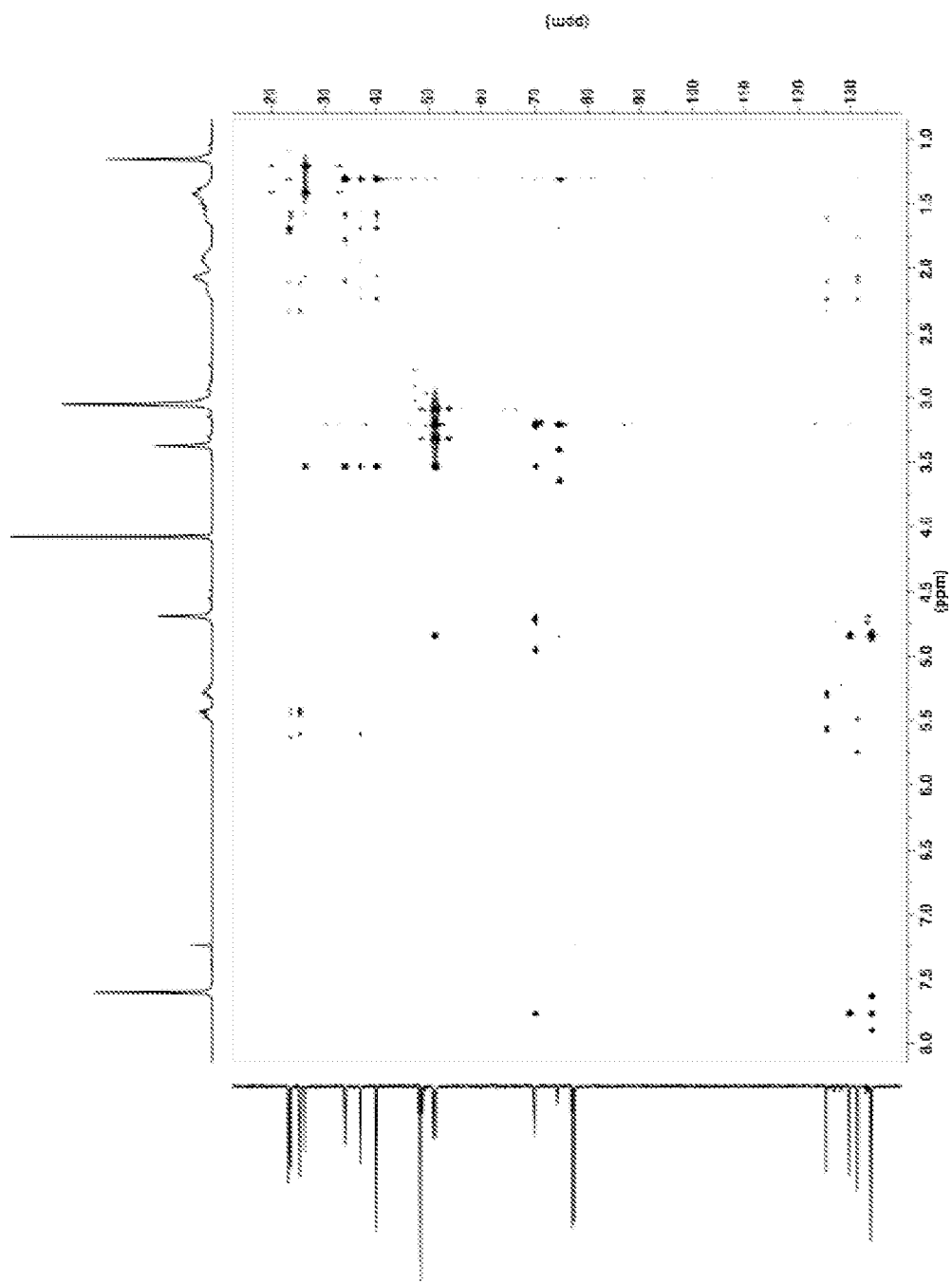
FIG. 13. gHMBC NMR spectrum of Monomer 2.
Figure 18:
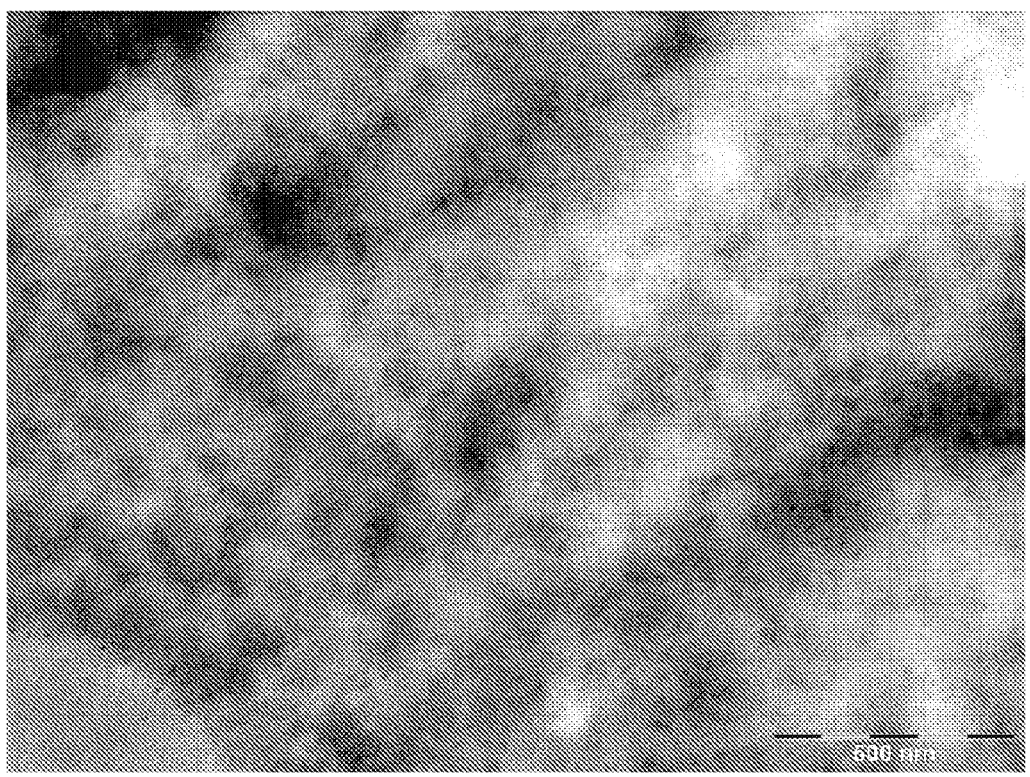
FIG. 18. Additional TEM image with larger window than that shown in FIG. 6c.

A general scheme of the complete synthesis of Monomer 2 as shown in FIG. 11.

Preparation of (Z)-tert-butyl-cyclooct-4-enecarboxylate (B). This was prepared using a modified known procedure. Tert-butyl alcohol (9.80 mL, 102 mmol), 1,5-cyclooctadiene (A, 20.0 mL, 163 mmol), toluene (9.8 mL), palladium (II) chloride (0.290 g, 1.64 mmol) and triphenylphosphine (1.71 g, 6.52 mmol) were combined in a Parr reactor equipped with an overhead stirrer and sealed. It was pressurized to 800 psig carbon monoxide and then vented down to 50 psig. This processes was repeated twice more to purge the reactor of air, then pressurized to 600 psig and heated to 90° C. with rapid stirring. After 12 hours, the pressure had fallen to 300 psig. It was repressurized to 600 psig and stirred for an additional 24 hours after which time it had decreased to 400 psig. It was cooled, vented and the yellow solution was washed into a flask with toluene and the volatiles were removed under vacuum. The yellow solution was distilled at 75-80° C. under dynamic vacuum with the receiving flask at −78° C. yielding a clear oil (17.7 g, 82%). $^1$H NMR (300 MHz, C6D6) δ 5.40-5.58 (2H, m), 2.24-2.40 (1H, m), 2.00-2.20 (2H, m), 1.70-1.95 (4H, m), 1.38-1.62 (3H, m), 1.24-1.36 (9H, s), 1.06-1.24 (1H, m). $^{13}$C NMR (75 MHz, C6D6) δ 176.68, 130.86, 130.34, 79.39, 44.96, 32.56, 30.16, 28.52, 28.46, 26.50, 24.89. HRMS EI (m/z): calc. for C13H22O2, 210.1620. found, 210.1621.

Synthesis of (Z)-tert-butyl-1-methylcyclooct-4-enecarboxylate (C). Diisopropylamine (13.9 mL, 99.2 mmol) was added to 160 mL dry tetrahydrofuran and cooled to 0° C. under flow of nitrogen. Butyllithium (62.0 mL, 99.2 mmol) was slowly added and then stirred for 20 minutes at 0° C. yielding a pale yellow solution that was then cooled to −78° C. A solution of compound B (19.0 g, 90.3 mmol) in 20 mL dry tetrahydrofuran was slowly added over 10 minutes via cannula. It stirred at −78° C. for 10 minutes and then slowly warmed to 0° C. over 30 minutes. Methyl iodide (11.3 mL, 181 mmol) was added and it stirred for 60 minutes at 0° C. The yellow solution was then opened to air and 90 mL of 8 M hydrochloric acid was slowly added while the solution was still cold, followed by extraction with diethyl ether (3×200 mL). The extracts were combined, washed with saturated sodium bicarbonate (2×100 mL), saturated sodium chloride (2×100 mL) and then dried with magnesium sulfate. Removing the solvent yielded a brown oil. (19.19 g, 95%). $^1$H NMR (300 MHz, C6D6) δ 5.59-5.70 (1H, m), 5.35-5.48 (1H, m), 2.19-2.40 (3H, m), 1.90-2.15 (2H, m), 1.65-1.83 (2H, m), 1.49-1.63 (1H, m), 1.35-1.49 (2H, m), 1.29-1.35 (9H, s), 1.05-1.10 (3H, s). $^{13}$C NMR (75 MHz, C6D6) δ 176.88, 132.61, 127.21, 79.50, 46.89, 36.62, 33.41, 28.40, 28.37, 26.45, 25.74, 25.28. HRMS EI (m/z): calc. for C14H24O2, 224.1776. found, 224.1771.

Preparation of (Z)-(1-methylcyclooct-4-enyl)methanol (D). Compound C (19.2 g, 85.6 mmol) was dissolved in 200 mL dry diethyl ether and cooled to 0° C. under flow of nitrogen in a Schlenk adapted round bottom flask equipped with an addition funnel. Lithium aluminum hydride (24.0 mL, 96.0 mmol) was transferred to the addition funnel via cannula and slowly added over 20 minutes turning the orange solution colorless. This was stirred at 0° C. for 2 hours and was then slowly warmed to room temperature. After stirring for 20 hours at room temperature, the colorless solution was cooled back to 0° C. and 20 mL of ethyl acetate was transferred to the addition funnel and then slowly added to the mixture until the solution turned cloudy. At this point the slurry was slowly poured over ~600 mL of ice. This stirred overnight forming a white slurry. Concentrated hydrochloric acid was slowly added to the solution until it became homogeneous. This was extracted with diethyl ether (3×200 mL). The ether extracts were washed with saturated sodium bicarbonate (200 mL) and saturated sodium chloride (200 mL). The resulting clear solution was dried with magnesium sulfate, filtered and the solvent removed in vacuo yielding the alcohol as a clear oil (13.1 g, 99%). $^1$H NMR (300 MHz, C6D6) δ 5.58-5.69 (1H, m), 5.37-5.49 (1H, m), 2.95-3.05 (2H, s), 1.90-2.20 (4H, m), 1.18-1.48 (7H, m), 0.75-0.81 (3H, s). $^{13}$C NMR (75 MHz, C6D6) δ 132.95, 126.83, 72.54, 39.36, 35.57, 30.98, 25.97, 25.63, 24.91, 23.32. HRMS EI (m/z): calc. for C10H18O, 154.1358. found, 154.1363.

Preparation of (Z)-1-methylcyclooct-4-enecarbaldehyde (E). Prepared using an adapted known procedure (caution, very foul-smelling reaction). Oxalyl chloride (7.88 mL, 93.1 mmol) was added to 200 mL of dichloromethane in a 500 mL round bottom flask and cooled to −78° C. Fresh dimethyl sulfoxide (13.2 mL, 186 mmol) was slowly added over 3 minutes resulting in a large amount of gas evolution. This colorless solution was stirred for 10 minutes. Compound D (13.1 g, 84.7 mmol) in 80 mL dichloromethane was added to the solution, and this stirred for 20 minutes at −78° C., which yielded a white non-viscous solution. Addition of triethylamine (118 mL, 847 mmol) with 40 mL dichloromethane yielded a white viscous slurry. This was kept at −78° C. for 10 minutes and then allowed to warm to room temperature over 60 minutes. The slurry was washed with water (3×400 mL) and dried with magnesium sulfate. Removing the solvent yielded a yellow oil (12.1 g, 94%). 1H NMR (300 MHz, C6D6) δ 9.10-9.13 (1H, s), 5.43-5.53 (1H, m), 5.25-5.38 (1H, q), 1.81-2.02 (4H, m), 1.70-1.81 (1H, m), 1.41-1.53 (1H, m), 1.21-1.41 (4H, m), 0.60-0.69 (3H, s). 13C NMR (75 MHz, C6D6) δ 204.84, 132.13, 127.09, 49.14, 33.52, 29.56, 25.82, 25.33, 24.40, 22.09. HRMS EI (m/z): calc. for C10H16O, 152.1201. found, 152.1200.

Synthesis of (Z)—N,N-dimethyl-1-(1-methylcyclooct-4-enyl)methanamine (F). Dimethylamine (80 mL, 160 mmol) was directly added to compound E (12.1 g, 79.4 mmol) in a 250 mL round bottom flask forming a clear orange solution. After stirring at room temperature for 5 hours with no observable change, the solution was transferred to a large beaker with 300 mL tetrahydrofuran and sodium triacetoxyborohydride (25.2 g, 119 mmol) was then added while stirring, which formed an orange non-viscous slurry. 400 mL diethyl ether was added after stirring for 22 hours to aid clean separation of the organic and aqueous fractions. 1 M hydrochloric acid (2×200 mL) was added to protonate the amine to separate it from any alcohol impurities (D). After isolating the aqueous fractions, 450 mL of 1 M potassium hydroxide was added to regenerate the amine, and the solution was extracted with diethyl ether (3×150 mL). The extracts were combined, washed with water (2×200 mL) and dried with magnesium sulfate. Removing the solvent yielded a pale yellow oil (8.2 g, 57%). $^1$H NMR (300 MHz, C6D6) δ 5.62-5.72 (1H, m), 5.40-5.54 (1H, m), 2.20-2.38 (1H, m), 1.95-2.20 (9H, m), 1.85-1.95 (2H, d), 1.24-1.62 (6H, m), 1.86-1.92 (3H, s). $^{13}$C NMR (75 MHz, C6D6) δ 133.10, 126.41, 71.38, 49.47, 40.11, 36.55, 32.47, 26.47, 25.66, 25.01, 24.79. HRMS EI (m/z): calc. for C12H23N, 181.1830. found, 181.1836.

Preparation of Monomer 2. Compound F (2.11 g, 11.6 mmol) and ∝,∝'-dibromo-p-xylene (1.40 g, 5.30 mmol) were combined with 15 mL of acetonitrile in a 100 mL round bottom flask and heated to 70° C., which briefly led to a homogeneous solution before a white precipitate formed. It was held at 70° C. with vigorous stirring for 19 hours and was then poured into 300 mL of diethyl ether to precipitate the product and wash away unreacted organics. The solution was filtered and the pale yellow solid was washed with an additional 200 mL of diethyl ether. Drying the solid overnight under vacuum at 50° C. furnished a pale yellow powder (3.16 g, 95%). Anal. calc. for C32H54N2Br2: C, 61.34; H, 8.69; N, 4.47; Br, 25.50. Anal. found: C, 61.08; H, 8.90; N, 4.47; Br, 25.45.

Sample procedure for copolymerization/film formation with the optimized composition for maximum conductivity. Monomer 2 (105 mg, 0.168 mmol) and COE (30 μL, 0.230 mmol) were combined and dissolved in a methanol/chloroform cosolvent (1.3 mL/2.0 mL, respectively). Grubbs' 2nd Generation catalyst (5.4 mg, 0.0064 mmol) was added and the solution was stirred vigorously for one minute to ensure homogeneity, and then transferred to a preheated (35° C.) metal dish (fluoropolymer-lined, diameter of 5.25 cm and depth of 3.0 cm) on top of a hot plate equipped with a metal plate to ensure uniform heating. This was covered with a round glass cover with a diameter of 7 cm and volume of 550 mL bearing two Kontes glass valves on top to control the rate of solvent evaporation. After one hour, the film had become a cloudy solid. At this time, the cover was removed and the film was kept at 35° C. for an additional hour, during which time the film becomes translucent as the solvent evaporates. The temperature was then turned up to 70° C. for 75 minutes. Following this, water was added and the translucent film is left to sit overnight, during which time, the film releases from the dish. Films were soaked in deionized water for at least 24 hours prior to hydroxide ion exchange.

For the series studying the impact of COE: Monomer 2, all reagents, catalyst and solvent amounts, and the procedure listed above were held constant while the COE amount was varied. The COE amounts used for each ratio are shown in FIG. 14 as well as the resulting conductivity values.

For the series studying the impact of catalyst loading, the solvent loading was the same as listed above, and a 2:1 loading of COE: Monomer 2 (40 μL COE, 0.307 mmol; 105 mg compound 1, 0.168 mmol) was used. The catalyst loading was varied accordingly and FIG. 15 displays the amounts of catalyst used for each ratio as well as the resulting conductivity values. To make thinner membranes of a desired composition, the ratios of reagents to solvent and catalyst was held constant and scaled back accordingly. For example, to cut the film thickness by roughly half, the amount of solvent, reagents and catalyst was cut by half. A film with the ratios of 50:1 (moles of olefin:catalyst) and 2:1 (COE:Monomer 2) was used for swelling measurements. When immersed into 8 M and 10 M preheated solutions of methanol in water and held at 60° C. for 2 hours, there was no detectable swelling. When immersed into the 12 M solution, the film samples exhibited an 8% volume increase.

Results and Discussion

Figure 6:
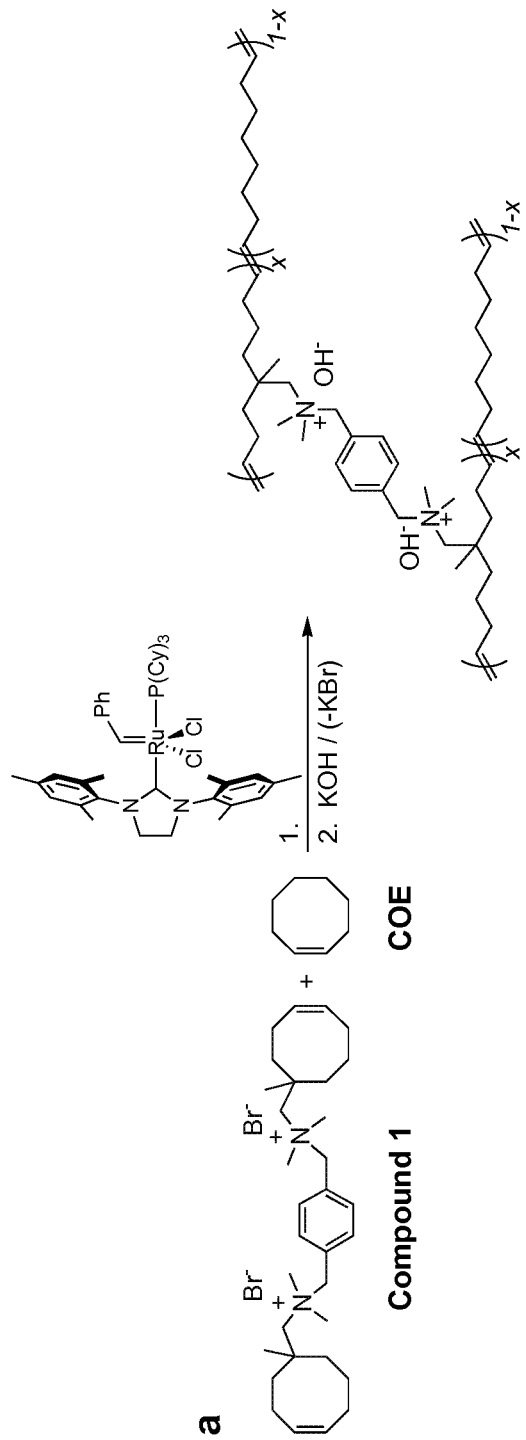
FIG. 6. Example of monomer structure and film synthesis. (a) General AAEM synthesis includes combining Monomer 2 (shown as Compound 1 in the figure) and (cyclooctene) COE in a chloroform/methanol cosolvent. Addition of Grubbs' $2^{nd}$ Generation catalyst, followed by transfer to the metal dish at 35° C., and subsequent hydroxide ion exchange furnishes the desired AAEM. (b) Photograph of film in the bromide form placed on top of a ruler to demonstrate the clarity of films. (c) TEM of film in the bromide form showing a featureless, amorphous morphology.
Figure 6:
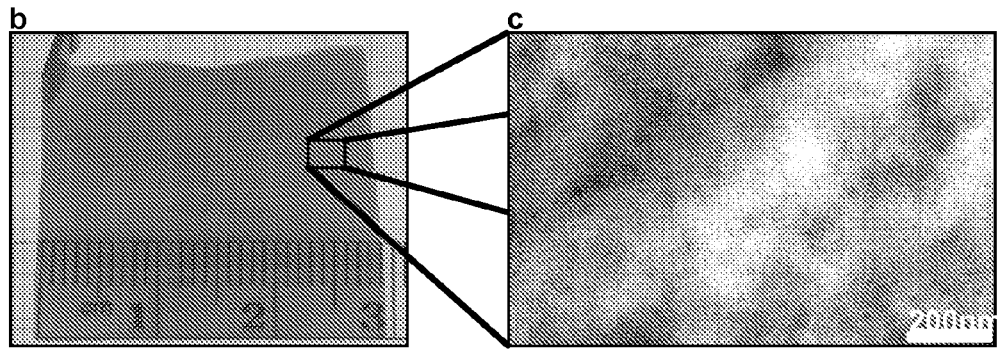

We prepared a variety of tetraalkylammonium-functionalized crosslinkers (two ammonium units and two olefins within the same molecule), such as Monomer 2 (FIG. 6 (a)), to enable crosslinking without the need for dicyclopentadiene; the use of the latter detracts from the ionic concentration, and therefore the conductivity of the material. Monomer 2 is readily synthesized in good yields from inexpensive starting materials, is readily scalable and the dication salt is easily separated from organic impurities. Furthermore, polymerization using Grubbs' air-stable $2^{nd}$ Generation catalyst eliminates the need for air and moisture free conditions during film casting, greatly simplifying membrane preparation. We polymerized Monomer 2 during a slow evaporation process, which led to uniform translucent thin films in near quantitative yields. Upon conversion to the hydroxide form, these materials became weak and difficult to handle. However, unlike materials developed from non-crosslinkable ammonium-functionalized cyclooctene monomers (analogous to Monomer 2 without the benzyl crosslinker), these materials would swell in water rather than dissolving, suggesting that crosslinking occurred upon polymerization of Monomer 2.

We found that addition of cyclooctene (COE) as a comonomer greatly improved the mechanical properties of the thin films. Subsequent conversion of the films from the bromide form to the hydroxide form led to no discoloration, furnishing the final AAEM as a translucent pale brown thin film (FIG. 6 (*b*)). FIG. 6 (*c*) is a transmission electron micrograph of the amorphous material in the bromide form, which shows only random aggregations and no signs of well ordered structure implying that these materials contain a relatively uniform distribution of tetraalkylammonium cations. Furthermore, differential scanning calorimetry analysis of the thin films in the bromide form revealed no melting temperature whereas polycycloctene produced using Grubbs $2^{nd}$ Generation catalyst showed a melting temperature of 37° C. This supports the random incorporation of Monomer 2 and COE into the crosslinked polymer architecture. In an effort to maximize performance and gain a better understanding for this system, we prepared a variety of copolymers and studied their resulting mechanical properties and conductivites.

Figure 7:
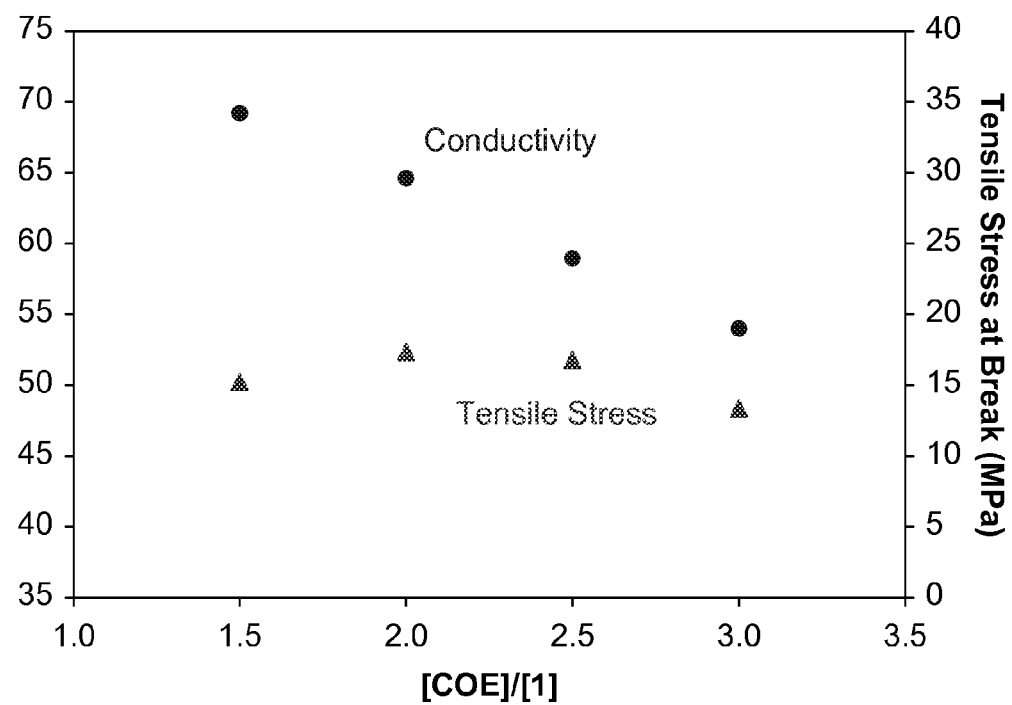
FIG. 7. Data showing the influence of COE loading on conductivity and material properties at 22° C. Conductivity values (●) were obtained from measurements of two separate films of the same composition and averaged. All films had a [Monomer 2] (shown as [1] in figure):[catalyst] loading of 25:1. Tensile stress values (▲) are an average of multiple measurements with error bars omitted for clarity. All tensile stress errors are ±4.2 MPa or less and calculated at the 95% confidence level.

The relationship between the ratio of COE to 1 and hydroxide conductivity at room temperature is shown in FIG. 7. The trend displays a maximum conductivity of 69 mS/cm with a composition of 1.5:1 molar equivalents of COE to Monomer 2. Higher loadings of Monomer 2 yielded materials with insufficient mechanical integrity for reliable measurements when pressed into the conductivity clamp. Diminished conductivity at higher COE loadings was expected because the ion concentration within the polymer membrane is decreased. The correlation between tensile strength and COE loading is also shown in FIG. 7. Mechanical properties began to degrade as the composition moved below 2 equivalents of COE and rapidly dropped off below 1.5 equivalents. Increasing beyond 2 equivalents of COE to Monomer 2 decreased the tensile strength, presumably because the crosslink density decreased as well. The overall trend between the two relationships shown in FIG. 7 is noteworthy because it implies that there is a significant correlation between mechanical properties and conductivity.

Figures 8, 9:
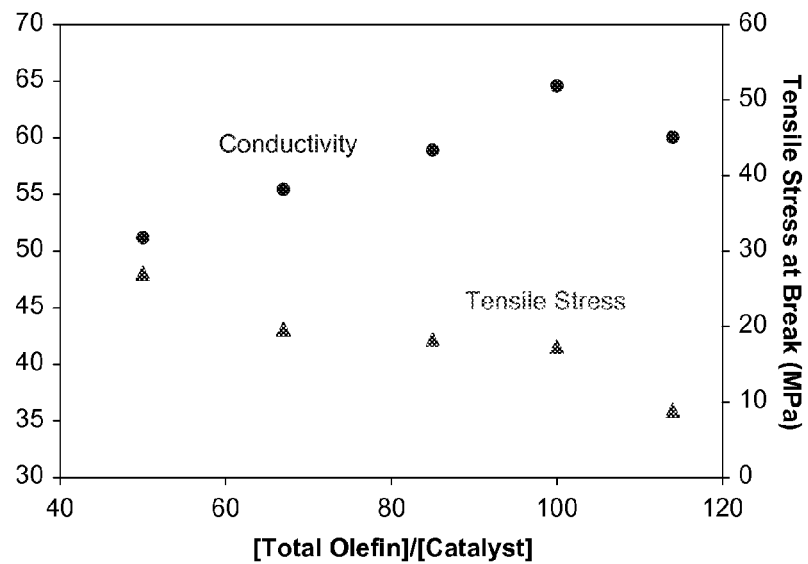
FIG. 8. Data showing the influence of catalyst loading on conductivity and material properties at 22° C. Conductivity values (●) were obtained from measurements of two separate films of the same composition and averaged. All films have a [COE]:[Monomer 2] loading of 2:1. Tensile stress values (▲) are an average of multiple measurements with error bars omitted for clarity. All tensile stress errors are ±4.2 MPa or less and calculated at the 95% confidence level.
FIG. 9. Data showing conductivity dependence upon counter ion. All films had the composition of 1.5:1 [COE]:[Monomer 2] with [total olefin]:[catalyst] loading of 90:1. Errors calculated at the 95% confidence level.

This correlation was further supported when we investigated the impact of catalyst loading on conductivity and mechanical properties (FIG. 8). Conductivity generally increased with decreased catalyst loading. However, when the monomer to catalyst ratio was increased above 100:1 moles of olefin to moles of catalyst, the material became brittle and the conductivity rapidly decreased. This loss of mechanical properties and subsequent conductivity reduction is likely attributable to excessive swelling, which occurs when there is insufficient crosslink density to resist osmotic pressure. Water uptake measurements act as a valuable aid in evaluating crosslink density. For the AAEMs with low catalyst loading, water uptake as high as 225% was observed, whereas increasing catalyst loading to increase crosslink density diminished water uptake nearly two-fold. Increased crosslinking improves the mechanical strength of the membrane, but decreases the conductivity, which is a commonly observed trend.

These materials are very promising candidates for fuel cell applications because they exhibit high hydroxide ion conductivity with desirable material properties. We postulate that these conductivities and mechanical properties are a direct result of crosslinking enabling high ion content. A considerable benefit of this system is that it is highly tunable for the desired application. For example, films with lower crosslink density can be synthesized to maximize conductivity when a fuel like hydrogen is used and swelling is less problematic. By contrast, COE loading can be varied to improve the material properties and higher crosslinking densities can be installed to combat swelling when carbon-based fuels are employed. Notably, there is no observable swelling of our AAEMs with high crosslink densities when immersed in 10 molar aqueous methanol at 60° C. All direct methanol fuel cells known to the authors, regardless of the concentration of methanol in the fuel reservoir, expose the electrolyte to only dilute aqueous methanol solutions of 1 molar concentration or lower, a value that is one order of magnitude below this system's tolerance. This is a very significant attribute for this system because using more concentrated fuels leads to higher energy densities. Altering the quantities of reagents used controls the film thickness, and films can be reproducibly made as thin as 30 μm in the hydroxide form. While thinner films can be generated, self-adhesion can be problematic when handling these materials.

To further investigate the capability of this system, we prepared films with an optimized ratio of the comonomers ([COE]:[Monomer 2]=1.5:1) and catalyst loading ([total olefin]:[catalyst]=90:1) to maximize conductivity of the polymer membrane. FIG. 9 shows the conductivities for the bromide, chloride, carbonate, bicarbonate and hydroxide forms of this composition at room temperature and at 50° C., demonstrating the desirable conductivity and scope of this system. Furthermore, if carbonate and bicarbonate species should form in the membrane under operating conditions, the conductivities of our system are still significant suggesting that performance losses will not be detrimental to overall performance. Indeed, it has even been shown that power densities can be as good or better when $CO_2$ is introduced into an AFC due to improved electrode kinetics in the presence of carbonate. The ion exchange capacity of the material is 2.3±0.2 mmol $OH^-$/g material which compares favorably to the theoretical value (2.8 mmol $OH^-$/g material), indicating that crosslinking enables high ion incorporation.

Figure 10:
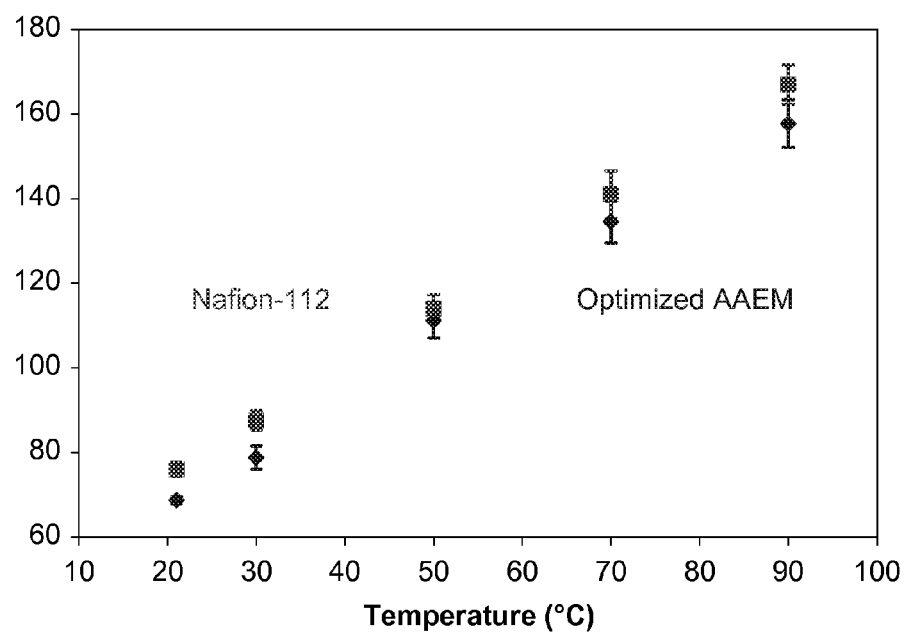
FIG. 10. Data showing the impact of temperature on conductivity. Conductivities of Nafion-112 (■) and of the optimized AAEM (♦), which has a [COE]: [Monomer 2] loading of 1.5:1 and [total olefin]:[catalyst] loading of 90:1 are shown. Errors are calculated at the 95% confidence level.

FIG. 10 illustrates the correlation between conductivity and temperature for Nafion 112 (measured using our experimental set up, which correlates well with literature values) and our AAEM with the composition optimized for conductivity. The conductivity of our AAEM material steadily increases with temperature and exhibits conductivities comparable to Nafion up to 90° C. when immersed in water. These hydroxide conductivities are higher than any reported AAEMs to date and demonstrate the potential of this system. When one considers that the mobility of protons is inherently faster than that of hydroxide ions in dilute solution by a factor of 1.77, it is even more impressive that our AAEM material conducts hydroxide ions nearly as well as Nafion conducts protons over this temperature range. The long term stability of AAEMs is generally of concern due to known degradation pathways for tetraalkylammonium ions under alkaline conditions (β-hydrogen elimination, direct nucleophilic substitution at an ∝-carbon or nitrogen glide formation).

It is expected that these materials will exhibit desirable durability because the tetraalkylammonium ions are devoid of β-hydrogens. Additionally, the high ion content of these materials makes them very hydrophilic, which will help retain water within the membrane to reduce the reactivity of the hydroxide ions, promote conductivity and protect the ammonium ions. More importantly, the high conductivity of this system will facilitate low temperature fuel cell operation, greatly diminishing degradation rates.

Conclusions

We have successfully developed a facile route for AAEM synthesis that provides multiple points of variation to allow tuning of the system for the desired application. These AAEMs exhibit high hydroxide ion conductivity, while retaining desirable mechanical strength, making them attractive candidates for fuel cell applications.

Example 3

Synthesis and Characterization of ISOM Monomer and Ionomers of the Present Invention General Methods and Materials All reactions and manipulations of compounds were carried out in air unless otherwise specified. Dimethylamine (2.0 M solution in tetrahydrofuran), sodium triacetoxyborohydride, potassium hydroxide, potassium bicarbonate, potassium carbonate, tert-butyl alcohol, oxalyl chloride (98%), triethylamine, cis-cyclooctene (95%), Grubbs' 2nd Generation catalyst, benzylidene[1,3-bis(2,4,6-trimethylphenyl)-2-imidazolidinylidene]dichloro(tricyclohexylphosphine)ruthenium (CAS: [246047-72-3]), Crabtree's catalyst, (1,5-Cyclooctadiene)(pyridine)(tricyclohexylphosphine)-Ir (I) PF6 (CAS: [64536-78-3]), standardized hydrochloric acid (0.1014 M) and standardized potassium hydroxide (0.1000±0.0001 M) were purchased from Sigma-Aldrich and used as received. 1,5-Cyclooctadiene (99%), n-butyllithium (1.6 M solution in hexanes), methyl iodide (99%), and lithium aluminum hydride (4.0 M solution in diethyl ether) were all purchased from Acros Organics and used as received. Diisopropylamine was purchased from Sigma-Aldrich and vacuum transferred from calcium hydride. All solvents were purchased from Sigma-Aldrich or Mallinckrodt. Tetrahydrofuran and diethyl ether were dried by passage over an alumina packed drying column. Hydrogen (99.99%) was purchased from Airgas. Palladium (II) chloride and calcium hydride were purchased from Strem Chemicals.

Small Molecule and Polymer Characterization $^1$H and $^{13}$C NMR spectra were recorded on Varian MERCURY 300 (1H, 300 MHz, $^{13}$C, 75 MHz) or Varian NOVA 600 ($^1$H, 600 MHz, $^{13}$C, 151 MHz) NMR spectrometers and referenced to C6HD5/C6D6 (7.16/128.39 ppm), CHCl3/CDCl3 (7.24/77.23 ppm), (D3C)2NCHO (8.03 ppm) or HDO (4.80 ppm). Mass spectra were acquired using a JEOL GCMate II mass spectrometer operating at 3000 resolving power for high resolution measurements in positive ion mode and an electron ionization potential of 70 eV. Samples were introduced via a GC inlet using an Agilent HP 6890N GC equipped with a 30 m (0.25 μm i.d.) HP-5 ms capillary GC column. The carrier gas was helium with a flow rate of 1 mL/min. Samples were introduced into the GC using a split/splitless injector at 230° C. with a split ratio of 10:1. Elemental analysis was performed by Robertson Microlit Laboratories, Inc. Madison, N.J.

Alkaline Anion Exchange Membrane (AAEM) Characterization

Ion exchange capacities (IECs) were determined using standard back titration methods. The thin film as synthesized (in iodide form) was dried under full vacuum overnight at 100° C. in order to completely dehydrate it and then weighed. Conversion to the hydroxide form was achieved by immersing the film in 3×60 mL portions of 1 M potassium hydroxide for 20 minutes each. Residual potassium hydroxide was washed away by immersing the membrane in 3×125 mL portions of deionized water for 20 minutes each. The AAEM was then stirred in 20 mL standardized 0.1 M $HCl_{(aq)}$ solution for 24 hours followed by titration with standardized 0.1 M $KOH_{(aq)}$ to determine the equivalence point. Control acid samples (with no AAEM present) were also titrated with standardized 0.1 M $KOH_{(aq)}$, and the difference between the volume required to titrate the control and the sample was used to calculate the amount of hydroxide ions in the membrane. This was divided by the dried mass of the membrane (vide supra) to give an IEC value with the units mmol OH$^-$/g I$^-$.

Water uptake was measured by the mass change between the fully hydrated and dried AAEMs. Immediately following hydroxide ion exchange, a sample was dried with a paper towel and placed in a capped vial to ensure accurate weighing. The sample was then dried at 20° C. under vacuum for 17 hours and re-weighed. The water uptake percentage value was calculated by: WU=[(Mass$_{final}$−Mass$_{initial}$)/Mass$_{initial}$]*100.

The in-plane hydroxide conductivity of the AAEM sample was measured by four probe electrochemical impedance spectroscopy (EIS) using a Solartron 1280B electrochemical workstation along with ZPlot and ZView software. The conductivity cell was purchased from BekkTech LLC (Loveland, Colo.), and a helpful schematic and description of a similar experimental setup has been reported. A strip of the thin film in the iodide form (ca. 4 cm long×0.5 mm wide) was converted to the hydroxide form by immersing it in 3×30 mL portions of 1 M potassium hydroxide for 20 minutes each. Residual potassium hydroxide was washed away by immersing the membrane in 3×60 mL portions of deionized water for 20 minutes each. Aliquots of each of these water washings were removed and analyzed by inductively coupled plasma atomic emission spectrometry (ICP-AES) for potassium ions. ICP-AES was performed by the Cornell Nutrient Analysis Laboratories, Department of Crop and Soil Sciences, Cornell University using a CIROS model from Spectro Analytical Instruments, Inc. and the EPA 6010B method. Negligible potassium ions were detected in the aqueous sample by the third water washing; approximately equal to that detected in deionized water verifying complete removal of base and preventing falsely high hydroxide conductivities. The AAEM was then clamped into the cell using a Proto 6104 torque screwdriver set to 1 inch ounce and completely immersed in Millipore water (>18 MΩ·cm), at either 20° C. or 50° C., during the measurement time. EIS was performed by imposing a small sinusoidal (AC signal) voltage, 10 mV, across the membrane sample at frequencies between 20,000 Hz and 0.1 Hz (scanning from high to low frequencies) and measuring the resultant current response. Using a Bode plot, the frequency region over which the impedance had a constant value was checked, and the highest frequency measurement in the Nyquist plot was taken as the effective resistance of the membrane. This was then used to calculate the hydroxide conductivity by employing the following formula: σ=L/Z'·A where L is the length between sense electrodes (0.425 cm), Z' is the real impedance response at high frequency, and A is the membrane area available for hydroxide conduction (width·thickness). The dimensional measurements were performed using a digital micrometer (±0.001 mm) purchased from Marathon Watch Company Ltd. (Richmond Hill, ON).

The mechanical properties of the thin films in the iodide form were characterized using an Instron system (model 5566) (Instron Co., Canton, Mass.) using a 100 N static Lodge cell and Blue Hill software. The tensile strengths of the wet samples were measured in the iodide form.

A consistent treatment of the precision of the measurements has been conducted. All errors are determined from sample standard deviations. Confidence intervals are at the 95% confidence level based on the sample deviations and using the relevant student-t distribution (N−1 degrees of freedom, N is the number of samples tested for each composition).

The solubility of the AAEMs (in hydroxide form) was evaluated by immersing the washed samples (30 mg) in various solvents (6 mL). The solutions were immediately heated and the membranes kept at 50° C. for 48 hours after which their solubility was qualitatively evaluated and is summarized in FIGS. 23 and 24.

For transmission electron microscopy (TEM) analysis, a piece of the sample (in iodide form) was embedded in Tissue-Tek and brought into a cryochamber at −60° C. The samples were then ultramicrotomed on a Leica Ultracut to a thickness of ~60 nm and picked up on a 200 mesh copper TEM grid. Images were taken on an FEI Tecnai T-12 TWIN TEM.

Monomer Synthesis

Figure 27:
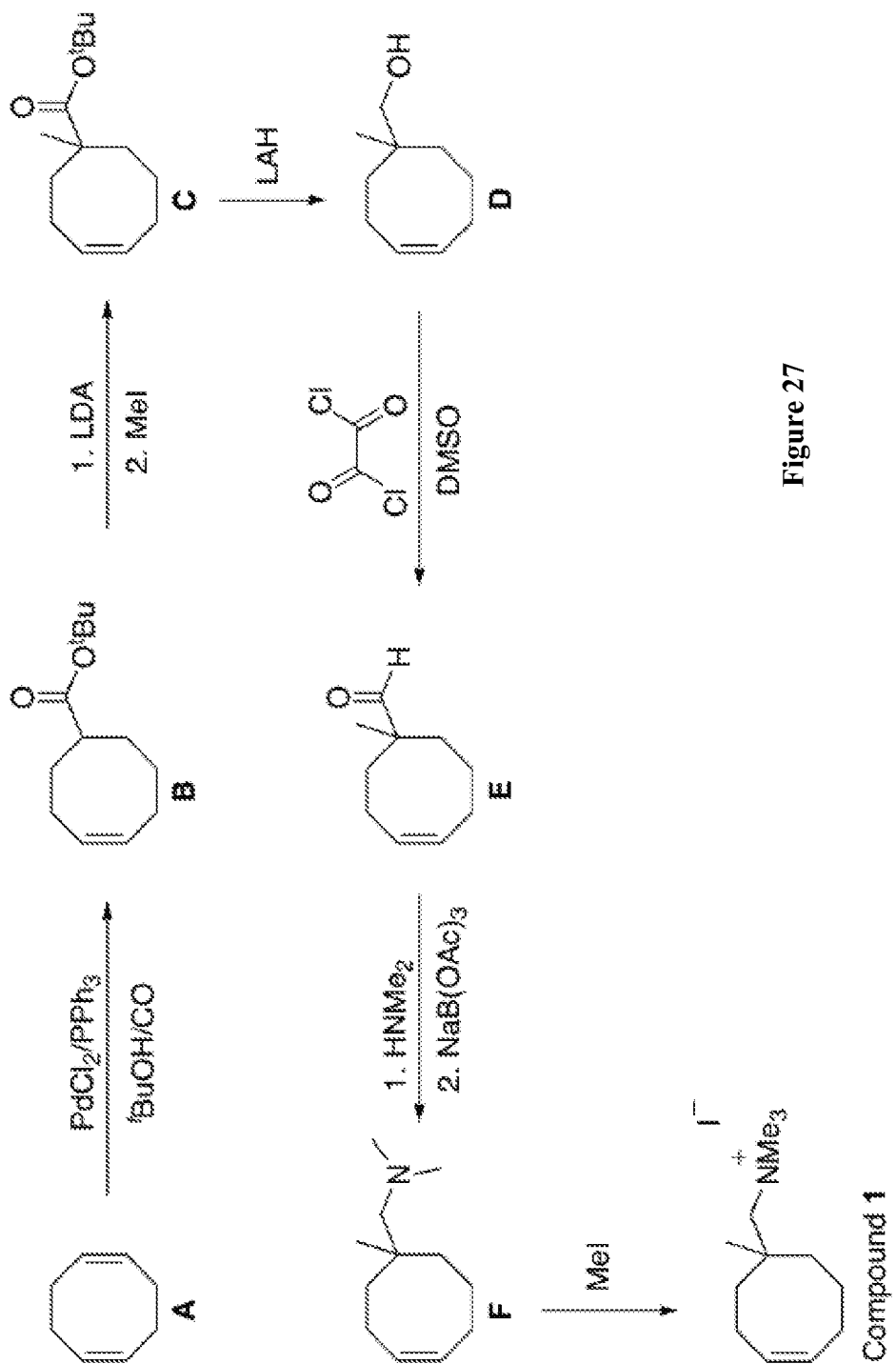
FIG. 27. Graphical representation of synthesis of Monomer 3 (shown as 1 in figure).
Figure 28:
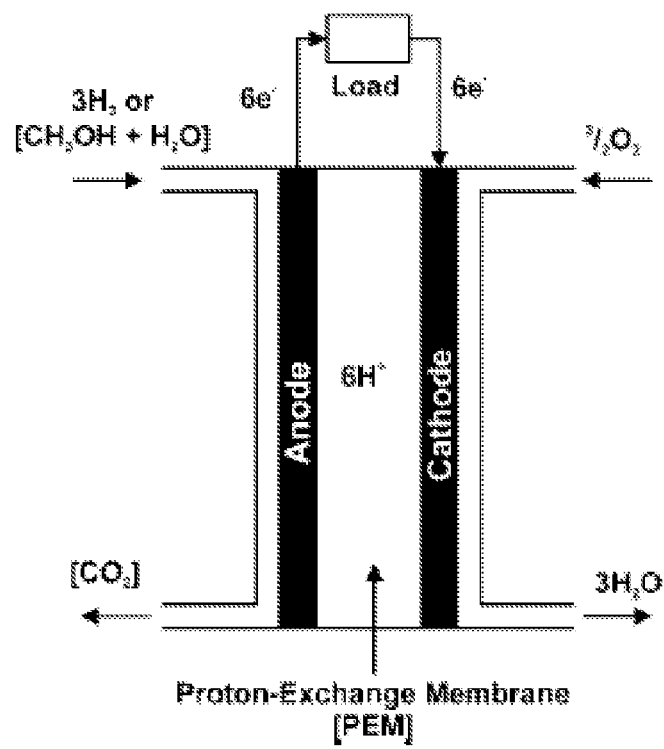
FIG. 28. Graphical representation of examples of (a) Proton-Exchange Membrane (PEM) and (b) Alkaline Anion-Exchange Membrane (AAEM) fuel cells.
Figure 28:
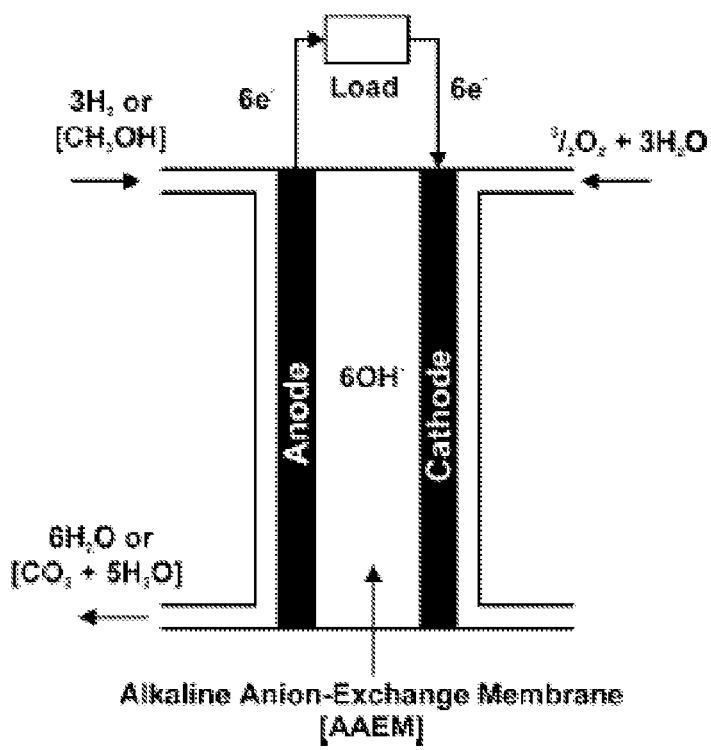

A general scheme of the complete synthesis of Monomer 3 is shown in FIG. 27.

Preparation of (Z)-tert-butyl-cyclooct-4-enecarboxylate (B). This compound was prepared using a modified literature procedure from Wagener and co-workers. Tert-butyl alcohol (9.80 mL, 102 mmol), 1,5-cyclooctadiene (A, 20.0 mL, 163 mmol), toluene (9.8 mL), palladium (II) chloride (0.290 g, 1.64 mmol) and triphenylphosphine (1.71 g, 6.52 mmol) were combined in a Parr reactor equipped with an overhead stirrer and sealed. The reactor was pressurized to 800 psig carbon monoxide and then vented down to 50 psig. This process was repeated twice more to purge the reactor of air, then pressurized to 600 psig and heated to 90° C. with rapid stirring. After 12 hours, the pressure had fallen to 300 psig. It was repressurized to 600 psig and stirred for an additional 24 hours after which time it had decreased to 400 psig. It was cooled, vented and the yellow solution washed into a flask with toluene and the volatiles were removed under vacuum. The yellow solution was distilled at 75-80° C. under dynamic vacuum with the receiving flask at −78° C. yielding a colorless oil (17.7 g, 82%). The NMR shifts closely match those in the aforementioned literature procedure. $^1$H NMR (300 MHz, C6D6) δ 5.40-5.58 (2H, m), 2.24-2.40 (1H, m), 2.00-2.20 (2H, m), 1.70-1.95 (4H, m), 1.38-1.62 (3H, m), 1.24-1.36 (9H, s), 1.06-1.24 (1H, m). $^{13}$C NMR (75 MHz, C6D6) δ 176.68, 130.86, 130.34, 79.39, 44.96, 32.56, 30.16, 28.52, 28.46, 26.50, 24.89. HRMS EI (m/z): calc. for C13H22O2, 210.1620. found, 210.1621.

Synthesis of (Z)-tert-butyl-1-methylcyclooct-4-enecarboxylate (C). Diisopropylamine (13.9 mL, 99.2 mmol) was added to 160 mL dry tetrahydrofuran and cooled to 0° C. under flow of nitrogen. A solution of n-butyllithium (62 mL, 1.6 M solution in hexanes, 99 mmol) was slowly added and then stirred for 20 minutes at 0° C. yielding a pale yellow solution that was then cooled to −78° C. A solution of compound B (19.0 g, 90.3 mmol) in 20 mL dry tetrahydrofuran was slowly added over 10 minutes via cannulation. The reaction mixture was stirred at −78° C. for 10 minutes and then slowly warmed to 0° C. over 30 minutes. Methyl iodide (11.3 mL, 181 mmol) was added and the reaction mixture allowed to stir for 60 minutes at 0° C. The yellow solution was then opened to the atmosphere and 90 mL of 8 M hydrochloric acid was slowly added while the solution was still cold, followed by extraction with diethyl ether (3×200 mL). The extracts were combined, washed with saturated sodium bicarbonate (2×100 mL), saturated sodium chloride (2×100 mL) and then dried with magnesium sulfate. Removing the solvent yielded a brown oil. (19.19 g, 95%). $^1$H NMR (300 MHz, C6D6) δ 5.59-5.70 (1H, m), 5.35-5.48 (1H, m), 2.19-2.40 (3H, m), 1.90-2.15 (2H, m), 1.65-1.83 (2H, m), 1.49-1.63 (1H, m), 1.35-1.49 (2H, m), 1.29-1.35 (9H, s), 1.05-1.10 (3H, s). $^{13}$C NMR (75 MHz, C6D6) δ 176.88, 132.61, 127.21, 79.50, 46.89, 36.62, 33.41, 28.40, 28.37, 26.45, 25.74, 25.28. HRMS EI (m/z): calc. for C14H24O2, 224.1776. found, 224.1771.

Preparation of (Z)-(1-methylcyclooct-4-enyl)methanol (D). Compound C (19.2 g, 85.6 mmol) was dissolved in 200 mL dry diethyl ether and cooled to 0° C. under a flow of nitrogen in a Schlenk adapted round bottom flask equipped with an addition funnel. Lithium aluminum hydride (24.0 mL, 96.0 mmol) was transferred to the addition funnel via cannulation and slowly added over 20 minutes turning the orange solution colorless. The solution was stirred at 0° C. for 2 hours and then slowly warmed to room temperature. After stirring for 20 hours at room temperature, the colorless solution was cooled back to 0° C. and 20 mL of ethyl acetate was transferred to the addition funnel and slowly added to the mixture until the solution turned cloudy. At this point the slurry was slowly poured over ~600 mL of ice with great caution and stirred overnight forming a white slurry. Concentrated hydrochloric acid was slowly added to the solution until it became homogeneous and then extracted with diethyl ether (3×200 mL). The ether extracts were washed with saturated sodium bicarbonate (200 mL) and saturated sodium chloride (200 mL). The resulting clear solution was dried with magnesium sulfate, filtered and the solvent removed in vacuo yielding the alcohol as a colorless oil (13.1 g, 99%). $^1$H NMR (300 MHz, C6D6) δ 5.58-5.69 (1H, m), 5.37-5.49 (1H, m), 2.95-3.05 (2H, s), 1.90-2.20 (4H, m), 1.18-1.48 (7H, m), 0.75-0.81 (3H, s). $^{13}$C NMR (75 MHz, C6D6) δ 132.95, 126.83, 72.54, 39.36, 35.57, 30.98, 25.97, 25.63, 24.91, 23.32. HRMS EI (m/z): calc. for C10H18O, 154.1358. found, 154.1363.

Preparation of (Z)-1-methylcyclooct-4-enecarbaldehyde (E). Prepared using a procedure adapted from Swern and coworkers; caution, very foul-smelling reaction. Oxalyl chloride (7.88 mL, 93.1 mmol) was added to 200 mL of dichloromethane in a 500 mL round bottom flask and cooled to −78° C. Fresh dimethyl sulfoxide (13.2 mL, 186 mmol) was slowly added over 3 minutes resulting in a large amount of gas evolution. This colorless solution was stirred for 10 minutes. A solution of compound D (13.1 g, 84.7 mmol) in 80 mL dichloromethane was added to the solution, and stirred for 20 minutes at −78° C. yielding a white solution. Addition of triethylamine (118 mL, 847 mmol) with 40 mL dichloromethane yielded a white viscous slurry. This mixture was kept at −78° C. for 10 minutes and then warmed to room temperature over 60 minutes. The slurry was washed with water (3×400 mL) and dried with magnesium sulfate. Removing the solvent afforded a yellow oil (12.1 g, 94%). $^1$H NMR (300 MHz, C6D6) δ 9.10-9.13 (1H, s), 5.43-5.53 (1H, m), 5.25-5.38 (1H, q), 1.81-2.02 (4H, m), 1.70-1.81 (1H, m), 1.41-1.53 (1H, m), 1.21-1.41 (4H, m), 0.60-0.69 (3H, s). $^{13}$C NMR (75 MHz, C6D6) δ 204.84, 132.13, 127.09, 49.14, 33.52, 29.56, 25.82, 25.33, 24.40, 22.09. HRMS EI (m/z): calc. for C10H16O, 152.1201. found, 152.1200.

Synthesis of (Z)—N,N-dimethyl-1-(1-methylcyclooct-4-enyl)methanamine (F). Dimethylamine (80 mL, 160 mmol) was directly added to compound E (12.1 g, 79.4 mmol) in a 250 mL round bottom flask forming a clear orange solution.

After stirring at room temperature for 5 hours with no observable change, the solution was transferred to a large beaker with 300 mL tetrahydrofuran. Sodium triacetoxyborohydride (25.2 g, 119 mmol) was then added with stirring, forming an orange slurry and was allowed to react for 22 hours. 400 mL diethyl ether was then added to aid clean separation of the organic and aqueous fractions. 1 M hydrochloric acid (2×200 mL) was added to protonate the amine in order to separate it from any alcohol impurities (D). After isolating the aqueous fractions, 450 mL of 1 M potassium hydroxide was added to regenerate the amine, and the solution was extracted with diethyl ether (3×150 mL). The extracts were combined, washed with water (2×200 mL) and dried with magnesium sulfate. Removing the solvent yielded a pale yellow oil (8.2 g, 57%). $^1$H NMR (300 MHz, C6D6) δ 5.62-5.72 (1H, m), 5.40-5.54 (1H, m), 2.20-2.38 (1H, m), 1.95-2.20 (9H, m), 1.85-1.95 (2H, d), 1.24-1.62 (6H, m), 1.86-1.92 (3H, s). $^{13}$C NMR (75 MHz, C6D6) δ 133.10, 126.41, 71.38, 49.47, 40.11, 36.55, 32.47, 26.47, 25.66, 25.01, 24.79. HRMS EI (m/z): calc. for C12H23N, 181.1830. found, 181.1836.

Preparation of Monomer 3. Compound F (3.00 g, 16.5 mmol) and methyl iodide (7.07 g, 49.5 mmol) were combined with 15 mL of acetonitrile in a 100 mL round bottom flask and heated to 80° C., which briefly gave a homogeneous solution before a white precipitate formed. The reaction mixture was held at 80° C. with vigorous stirring for 19 hours and then poured into 300 mL of diethyl ether to precipitate the product and wash away unreacted organics. The solution was then filtered and the pale yellow solid washed with an additional 200 mL of diethyl ether. Drying the solid overnight undervacuum at 100° C. furnished a faint yellow powder (5.07 g, 95%). $^1$H NMR (600 MHz, D2O) δ 6.11-6.17 (1H, m), 5.90-5.98 (1H, m), 3.68-3.94 (2H, m), 3.34-3.68 (9H, s), 2.47-2.82 (4H, d), 2.28-2.47 (1H, m), 1.83-2.23 (5H, m), 1.49-1.78 (3H, s). $^{13}$C NMR (151 MHz, D2O) δ 132.67, 126.40, 76.37, 56.28, 40.13, 36.72, 33.75, 25.97, 25.38, 24.14, 23.42. Anal. calc. for C13H$_{26}$NI: C, 48.30; H, 8.11; N, 4.33; I, 39.26. Anal. found: C, 48.38; H, 7.97; N, 4.28; I, 39.01.

Preparation of the Unsaturated Copolymer with 29 mol % Monomer 3. Monomer 3 (300 mg, 0.928 mmol) and COE (256 mg, 2.32 mmol) were combined and dissolved in a chloroform/methanol cosolvent (3 mL/0.3 mL, respectively). Grubbs' 2nd Generation catalyst (11 mg, 0.013 mmol) was added and the solution allowed to stir vigorously. After 1 hour, the cosolvent and unreacted COE were removed under vacuum, and the resulting polymer washed with chloroform. Drying overnight under vacuum at 100° C. furnished a brown solid (501 mg, 90%). $^1$H NMR (600 MHz, DMF-d7) δ 5.09-5.77 (6.5H, m), 3.32-3.91 (11H, m), 1.73-2.37 (13H, br m), 0.88-1.73 (28H, br m). $^{13}$C NMR (151 MHz, CDCl3/D3COD) δ 130.15, 74.64, 56.06, 38.96, 38.39, 32.62, 32.34, 29.44, 28.77, 27.01, 26.31, 24.78, 23.15.

Hydrogenation of the Unsaturated Copolymer with 29 mol % Monomer 3. The unsaturated copolymer with 29 mol % Monomer 3 (493 mg) was dissolved in a dichloromethane/methanol cosolvent (10 mL/5.0 mL, respectively) forming a light brown solution. The polymer solution and Crabtree's catalyst (4.7 mg, 0.0058 mmol) were combined in a Parr reactor equipped with an overhead stirrer and sealed. It was pressurized to 800 psig hydrogen and then vented down to 50 psig. This process was repeated twice more to purge the reactor of air, then pressurized to 800 psig and heated to 55° C. with rapid stirring. After 17 hours, it was cooled, vented and the swollen polymer gel dried under vacuum at 100° C. furnishing a yellow solid. (498 mg, 100%). $^1$H NMR (600 MHz, DMF-d7) δ 3.28-3.82 (11H, m), 1.00-1.76 (55H, br m). $^{13}$C NMR (151 MHz, CDCl3/D3COD) δ 74.67, 55.99 38.84, 29.98, 29.26, 24.69, 22.99.

Preparation of AAEM-29. The saturated copolymer with 29 mol % Monomer 3 (90 mg) was dissolved in a chloroform/methanol cosolvent (2 mL/1 mL, respectively) forming a light yellow solution and then transferred to a preheated (40° C.) metal dish (fluoropolymerlined, diameter of 5.25 cm and depth of 3.0 cm) on top of a hot plate covered with a metal plate to ensure uniform heating. The dish was covered with a round glass cover with a diameter of 7 cm and volume of 550 mL bearing one Kontes glass valve on top to control the rate of solvent evaporation. After one hour the cover was removed and the temperature was increased to 70° C. for another hour. Following this, water was added and the translucent film freely removed from the dish. The film was then soaked in deionized water for at least 24 hours prior to hydroxide ion exchange. The AAEM was generated as described above. To make thinner membranes the amount of polymer was scaled back accordingly.

Preparation of the Unsaturated Copolymer with 33 mol % Monomer 3. Monomer 3 (350 mg, 1.08 mmol) and COE (237 mg, 2.16 mmol) were combined and dissolved in a chloroform/methanol cosolvent (3 mL/0.4 mL, respectively). Grubbs' 2nd Generation catalyst (11 mg, 0.013 mmol) was added and the solution allowed to stir vigorously. After 1 hour, the cosolvent and unreacted COE were removed under vacuum, and the resulting polymer washed with chloroform. Drying overnight under vacuum at 100° C. furnished a brown solid (539 mg, 92%). $^1$H NMR (600 MHz, DMF-d7) δ 5.09-5.77 (6H, m), 3.32-3.91 (11H, m), 1.73-2.37 (12H, br m), 0.88-1.73 (26H, br m). $^{13}$C NMR (151 MHz, CDCl3/D3COD) δ 130.18, 74.52, 55.98, 38.98, 38.26, 32.67, 32.35, 29.45, 28.78, 27.02, 26.33, 24.74, 23.17.

Hydrogenation of the Unsaturated Copolymer with 33 mol % Monomer 3. The unsaturated copolymer with 33 mol % Monomer 3 (539 mg) was dissolved in a dichloromethane/methanol cosolvent (10 mL/5.0 mL, respectively) forming a light brown solution. The polymer solution and Crabtree's catalyst (4.8 mg, 0.0060 mmol) were combined in a Parr reactor equipped with an overhead stirrer and sealed. It was pressurized to 800 psig hydrogen and then vented down to 50 psig. This process was repeated twice more to purge the reactor of air, then pressurized to 800 psig and heated to 55° C. with rapid stirring. After 17 hours, it was cooled, vented and the swollen polymer gel dried under vacuum at 100° C. furnishing a yellow solid. (544 mg, 100%). $^1$H NMR (600 MHz, DMF-d7) δ 3.28-3.82 (11H, m), 1.00-1.76 (49H, br m). $^{13}$C NMR (151 MHz, CD3Cl/D3COD) δ 75.05, 56.04 38.90, 30.05, 29.52, 24.86, 23.16.

Preparation of the AAEM-33: The saturated copolymer with 33 mol % Monomer 3 (90 mg) was dissolved in a chloroform/methanol cosolvent (2 mL/1 mL, respectively) forming a light yellow solution and then transferred to a preheated (40° C.) metal dish (fluoropolymerlined, diameter of 5.25 cm and depth of 3.0 cm) on top of a hot plate covered with a metal plate to ensure uniform heating. The dish was covered with a round glass cover with a diameter of 7 cm and volume of 550 mL bearing one Kontes glass valve on top to control the rate of solvent evaporation. After one hour the cover was removed and the temperature was increased to 70° C. for another hour. Following this, water was added and the translucent film freely removed from the dish. The film was then soaked in deionized water for at least 24 hours prior to hydroxide ion exchange. The AAEM was generated as described above. To make thinner membranes the amount of polymer was scaled back accordingly.

Monomer 3 (FIG. 27) was readily synthesized from inexpensive starting materials. The lack of β-hydrogen atoms in 1 prevents Hofmann elimination degradation from occurring in the hydroxide form, increasing the ammonium ion stability. Additionally, trimethylammounium groups have been shown to be reasonably stable, exhibiting negligible degradation under alkaline conditions at elevated temperatures.

Figure 19:
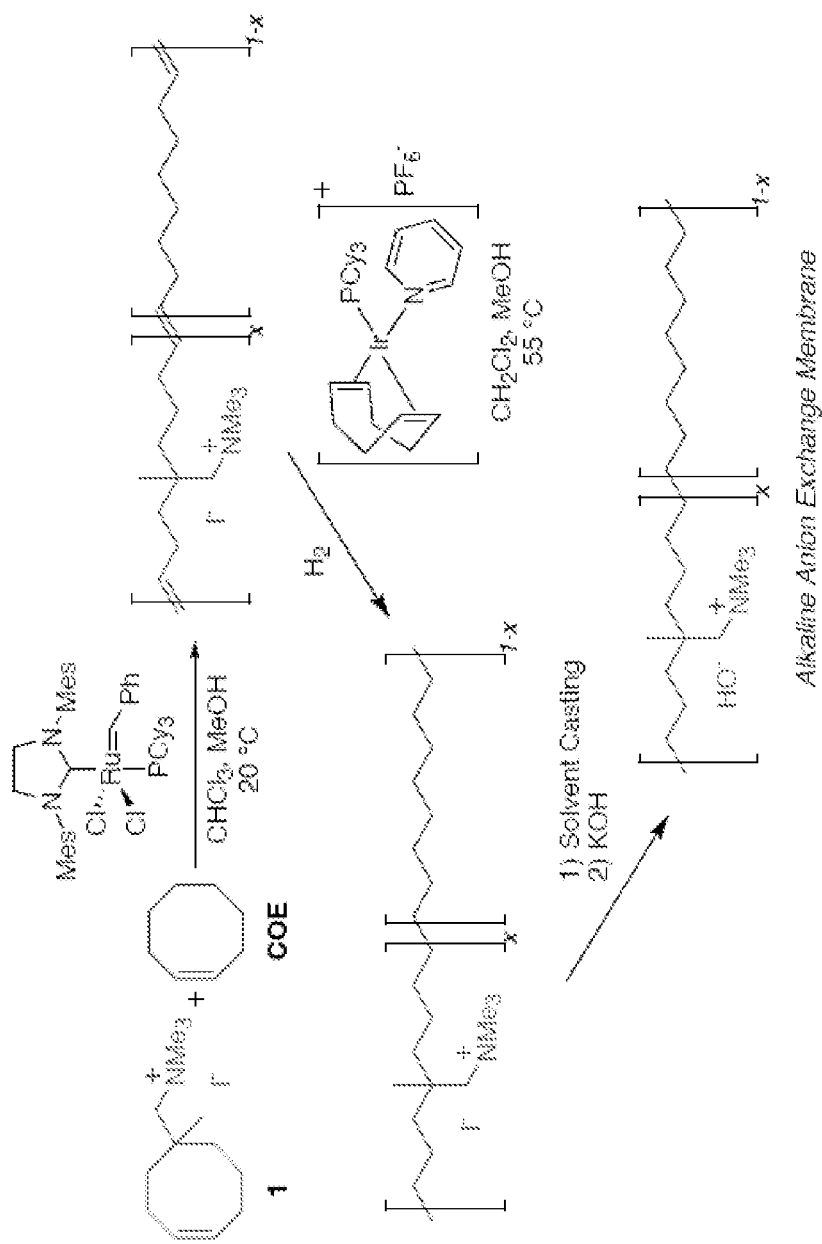
FIG. 19. Graphical depiction of synthesis scheme for an ionomer (Monomer 3—shown as 1 in figure) of the present invention.

We used ROMP to synthesize copolymers of varying composition by introducing Grubbs' 2nd Generation catalyst ([Ru]) to a chloroform/methanol solution of cyclooctene (COE) and Monomer 3 at 20° C. in air (FIG. 19). After 1 hour the solvents and unreacted COE were removed under vacuum, and the subsequent polymer washed with chloroform to remove unreacted Monomer 3 with yields exceeding 90%. The relative ratio of the two monomers (determined by $^1$H NMR spectroscopy) remains nearly constant throughout the reaction, indicative of a random copolymerization. These copolymers were cast into thin films and subsequently anion exchanged with potassium hydroxide to generate AAEMs, but unfortunately they displayed poor mechanical properties due to considerable swelling in water. Moreover, it has been previously noted that unsaturated polymers synthesized via ROMP may not be stable under ambient conditions for prolonged periods due to oxidative degradation, and this is critical as fuel cell membranes are exposed to harsh oxidizing and reducing conditions during operation. Therefore, all the unsaturated copolymer samples were hydrogenated to produce a saturated backbone with the expectation that these concerns over stability would be eliminated. It should be noted that even though oxidative radical degradation is a concern with hydrocarbon-based PEMs it has been shown that this degradation pathway is hindered under the highly alkaline conditions intrinsic to AAEM operation. Preparation of the saturated copolymers was accomplished by hydrogenating the polyolefins using Crabtree's catalyst ([COD]Ir(Py)(PCy$_3$)]PF$_6$, FIG. 19) and hydrogen gas. Quantitative conversion was typically complete within 17 hours as confirmed by the complete disappearance of olefinic resonances in the $^1$H NMR spectrum, effectively yielding tetraalkylammonium-functionalized polyethylene. Furthermore, it was expected that this polyethylene backbone would provide the hydrophobic support necessary for the high ion incorporation required to maximize conductivity without the detrimental loss of mechanical stability due to swelling.

Figure 25:
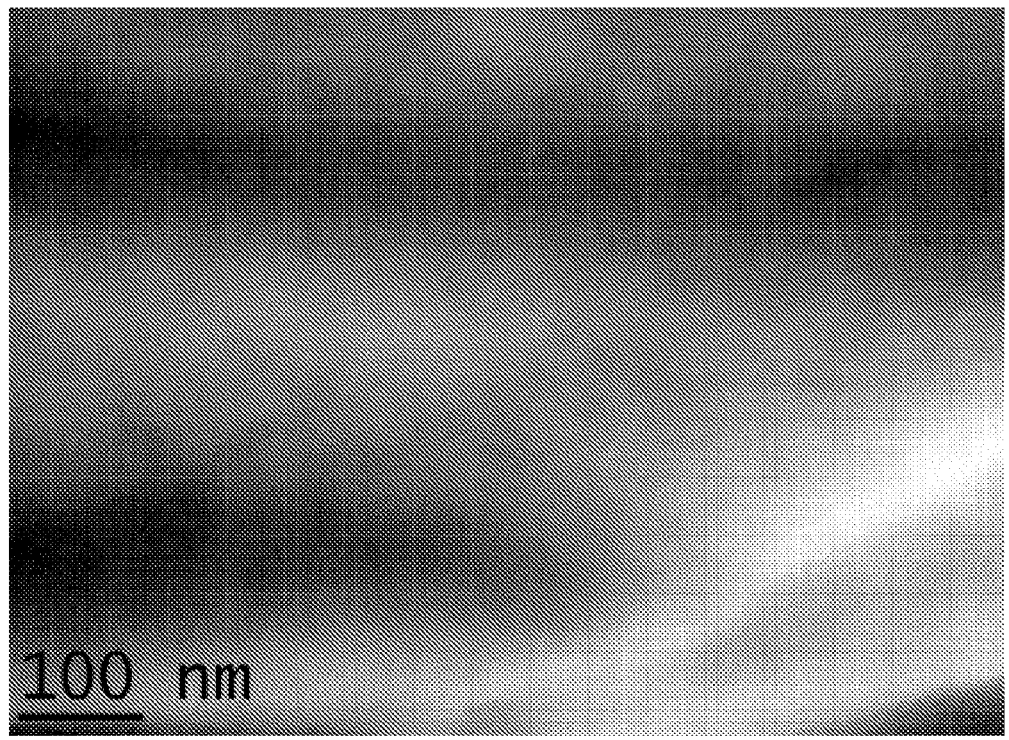
FIG. 25. TEM image of a saturated ionomer copolymer (in iodide form) with 29 mol % 1.
Figure 26:
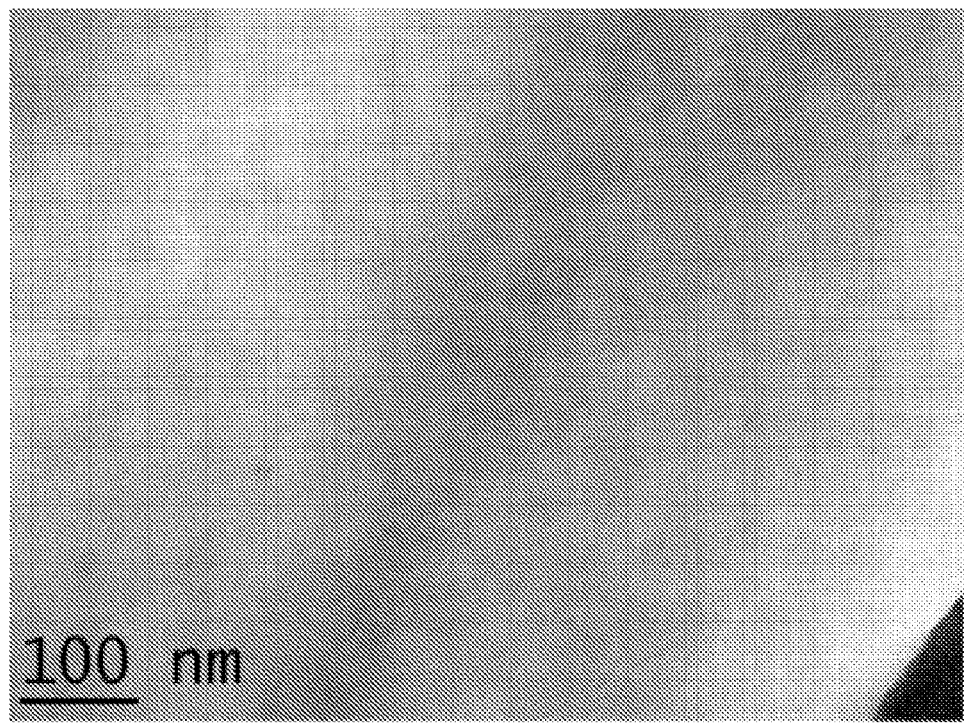
FIG. 26. TEM image of a saturated ionomer copolymer (in iodide form) with 33 mol % 1.

The hydrogenated copolymers in the iodide form were dissolved in a chloroform/methanol cosolvent and cast onto a fluoropolymer-lined metal dish preheated to 40° C. from which the volatiles were slowly evaporated. The films were removed from the dish and dried under vacuum to exhaustively remove residual solvent. Analysis of the thin films by transmission electron microscopy (TEM) revealed no microphase separation possibly suggesting a random distribution of tetraalkylammonium ions (see FIGS. 25 and 26). Ion exchange was accomplished by soaking the films in 1 M potassium hydroxide, furnishing transparent and nearly colorless AAEMs. Overall, the AAEMs are easily handled, exhibiting excellent flexibility and strength qualitatively similar to polyethylene. Typical film thicknesses ranged from 20-50 µm, however membranes as thin as 10 µm were synthesized without any loss in their mechanical integrity. Thinner AAEMs are desirable due to their decreased ionic resistance, resulting in increased fuel cell performance.

Figure 20:
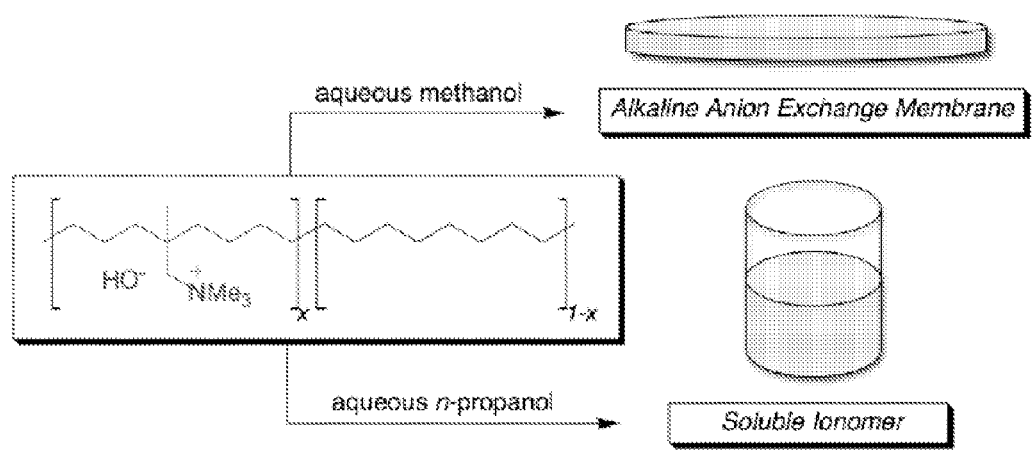
FIG. 20. Graphical depiction of preparation and example of use of an ionomer of the present invention.
Figure 21:
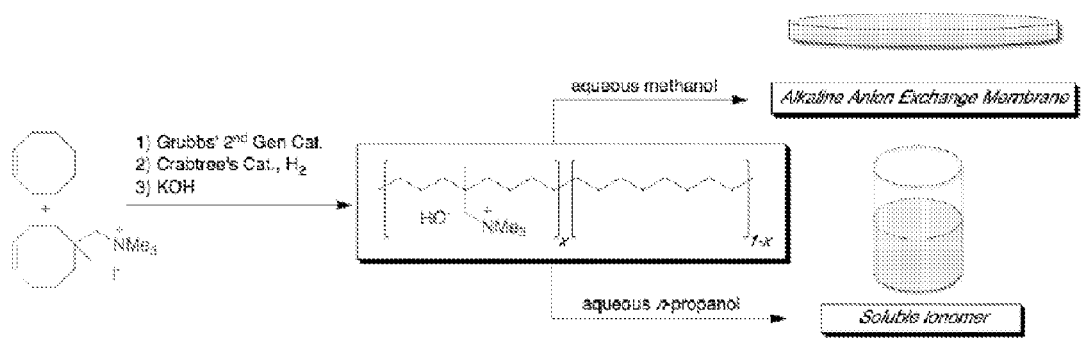
FIG. 21 Graphical depiction of AAEM and soluble ionomer (in certain solvents described herein) from a polymer. Example of solubility characteristics of the tetralkylammonium-functionalized polyethylene, which have desirable mechanical strength and hydroxide conductivity. Example of an ionomer of the present invention (e.g., a single polymer) that can be used as both an alkaline anion exchange membrane and ionomer interface material.

A significant challenge in alkaline fuel cell research is the development of an alkaline analogue of commercially available solutions of Nafion®. Nafion® is insoluble in water and aqueous methanol, but soluble in mixtures of other low boiling point solvents including ethanol and n-propanol. This solvent processability allows Nafion® to be impregnated into the electrocatalyst layers producing an ionomer interface material found in high performing PEM fuel cells. A critical consequence of this solvent processability is that the same polymer can be used as both the polymer electrolyte membrane and ionomer interface material. Remarkably, the AAEMs are completely insoluble in both pure water and aqueous methanol at 50° C. (50 vol. % water) allowing the use of methanol as a fuel, but exhibit excellent solubility in a variety of other aqueous alcohols (e.g., 20 wt % AAEM in aqueous n-propanol, 50 vol. % water, see FIGS. 23 and 24). This solvent processability (FIG. 20) is rare among AAEMs and potentially extends the utility of this system for use as both a fuel cell membrane and ionomer interface material from a single polymer, much like Nafion.

The optimized AAEMs, with respect to mechanical properties and hydroxide ion conductivity, had 29 (AAEM-29) or 33 (AAEM-33) mol % 1. Attempts to synthesize AAEMs with a higher mol % Monomer 3 led to materials with poor mechanical properties due to swelling, while increasing the mol % COE led to decreased hydroxide conductivity. Detailed characterization data for both optimized AAEM compositions is provided in FIG. 22. The ion exchange capacities (IECs) for AAEM-29 and AAEM-33 are 1.29 and 1.50 mmol OH–/g, respectively. These IECs are within the range of previously reported AAEMs and both commercial and non-commercial ionomer interface materials.

It has been shown that sufficient water uptake of AAEMs is needed to form interconnected hydrated domains thereby maximizing ion conductivity; however, excessive water uptake may also result in a detrimental loss of mechanical integrity. The gravimetric water uptake (WU) values of the optimized AAEMs were measured and as expected, increasing the ionicity of the AAEMs led to an increase in WU with AAEM-29 and AAEM-33 exhibiting WUs of 97% and 132%, respectively. These WU values exceed those of most current AAEMs, potentially leading to increased hydroxide ion conductivity; however, we were concerned that this would also result in poor mechanical properties.

Tensile stress-strain measurements were performed in order to evaluate the mechanical properties of both samples. AAEM-29 had a tensile strength at break of 9 MPa at a strain of 170%, while AAEM-33 sample showed a tensile strength at break of 6 MPa at a strain of 130%. These two classes of crosslinked materials demonstrate greater tensile strength at break but also show less strain at break. Nonetheless, this system certainly exhibits the mechanical strength required to function as a fuel cell membrane and underscores the ability of polyethylene to act as an effective hydrocarbon support.

The in-plane hydroxide conductivity for each film composition was measured at 20° C. and 50° C. AAEM-29 exhibits conductivities of 39 mS/cm at 20° C. and 56 mS/cm at 50° C. More impressively, AAEM-33 conducts at 47 mS/cm at 20° C. and 65 mS/cm at 50° C.

In order to investigate the effect of carbonation on membrane conductivity, AAEM-29 and AAEM-33 in their iodide form were converted to the carbonate form by immersing them in 1 M potassium bicarbonate. The in-plane carbonate conductivity for each film composition was measured at 20° C. and 50° C. AAEM-29 exhibits carbonate conductivities of 12 mS/cm at 20° C. and 29 mS/cm at 50° C. while AAEM-33 conducts at 13 mS/cm at 20° C. and 30 mS/cm at 50° C.

Although these results suggest decreased ionic conductivity after carbonation, other studies suggest this is not detrimental to fuel cell performance as hydroxide anions are continuously regenerated by oxygen reduction at the cathode.

As previously mentioned, a significant challenge in alkaline fuel cell research has been the development of an AAEM that is insoluble in water and aqueous methanol, but soluble in mixtures of other low boiling point solvents such as n-propanol. The current system displays excellent conductivities, is soluble in aqueous n-propanol (50 vol. % water) and is impressively insoluble in aqueous methanol (50 vol. % water).

In summary, we have developed a tetraalkylammonium functionalized polyethylene that exhibits excellent mechanical strength and remarkable hydroxide conductivity, in addition to being solvent processable. This solvent processability extends the potential utility of this system for use as both an AAEM and ionomer interface material.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. An ionomer comprising ionic strained olefin monomer (ISOM) units and optionally random or sequentially placed strained olefin monomer (SOM) units, having the following structure:

$$+ISOM+_x+SOM+_{1-x}$$

wherein the ISOM and SOM units are connected by carbon-carbon single bonds and/or carbon-carbon double bonds, wherein the ISOM unit has a non-aromatic hydrocarbon backbone and comprises one or more tetraalkylammonium groups connected to the backbone by an aliphatic polyatomic linkage or aliaromatic polyatomic linkage, and any carbon atoms in the beta position relative to an ammonium nitrogen do not bear hydrogen substituents, wherein the SOM unit is a non-aromatic hydrocarbon unit, wherein x is from 0.05 to 1.0, and wherein the SOM units or ISOM units are formed from SOMs or ISOMs, respectively, that have a strained ring or carbocyclic structure and an alkene moiety in a ring-opening metathesis polymerization.

2. The ionomer of claim 1, wherein the number average molecular weight of the ionomer, Mn, is from 5,000 to 1,000,000 g/mol and/or the weight average molecular weight of the ionomer, Mw, is from 5,000 to 2,000,000 g/mol.

3. The ionomer of claim 1, wherein the end groups of the ionomer are independently selected from $=CH_2$, $=CHR$ (where R is $CH_2W$ where W is H, alkyl, halide, hydroxide or acetate), $=CHPh$, $—CH_3$, $—CH_2R$ (where R is $CH_2W$ where W is H, alkyl, halide, hydroxide or acetate) and $—CH_2Ph$.

4. The ionomer of claim 1, wherein the ISOM and SOM units are connected by a carbon-carbon double bond and the ionomer has the following structure:

wherein $R^1$, $R^2$ and $R^3$ are each, independently, a $C_1$ to $C_{20}$ group, wherein if the $C_1$ to $C_{20}$ group has a carbon in the beta position relative to the ammonium nitrogen atom then the beta carbon of the $C_1$ to $C_{20}$ group does not have a hydrogen substituent, wherein $A^-$ is selected from halide, hydroxide, hexafluorophosphate, borate, carbonate, bicarbonate and carboxylate, and wherein x is from 0.05 to 1.0.

5. The ionomer of claim 1, wherein the ISOM and SOM units are connected by a carbon-carbon single bond and the ionomer has the following structure:

wherein $R^1$, $R^2$ and $R^3$ are each, independently, a $C_1$ to $C_{20}$ group, wherein if the $C_1$ to $C_{20}$ group has a carbon in the beta position relative to the ammonium nitrogen atom then the beta carbon of the $C_1$ to $C_{20}$ group does not have a hydrogen substituent, wherein $A^-$ is selected from halide, hydroxide, hexafluorophosphate, borate, carbonate, bicarbonate and carboxylate, and wherein x is from 0.05 to 1.

6. The ionomer of claim 1, wherein at least one first ISOM or SOM unit is connected by a polyatomic linking group (PAL) or aliaromatic polyatomic linkage comprising a $C_1$ to $C_{20}$ group, wherein if the $C_1$ to $C_{20}$ group has a carbon in the beta position relative to the ammonium nitrogen atom then the beta carbon of the $C_1$ to $C_{20}$ group does not have a hydrogen substituent, to a second ISOM or SOM unit, and wherein the second ISOM or SOM unit is in the same ionomer chain as the first ISOM or SOM unit or the second ISOM or SOM unit is a different ionomer chain than the first ISOM or SOM unit.

7. The ionomer of claim 6, wherein the ISOM and SOM units are connected by a carbon-carbon double bond and the ionomer has the following structure:

wherein $R^1$, $R^2$ and $R^3$ are, independently, a $C_1$ to $C_{20}$ group, wherein if the $C_1$ to $C_{20}$ group has a carbon in the beta position relative to the ammonium nitrogen atom then the beta carbon of the $C_1$ to $C_{20}$ group does not have a hydrogen substituent, wherein $R^4$ is a $C_1$ to $C_{20}$ group, wherein a first y unit is crosslinked to second y unit in a same or different ionomer chain than the first y unit, wherein $A^-$ is selected from halide, hydroxide, hexafluorophosphate, borate, carbonate, bicarbonate, and carboxylate, and wherein x is from 0.05 to 1 and x+y+z=1.

8. The ionomer of claim 6, wherein the ISOM and SOM units are connected by a carbon-carbon single bond and the ionomer has the following structure:

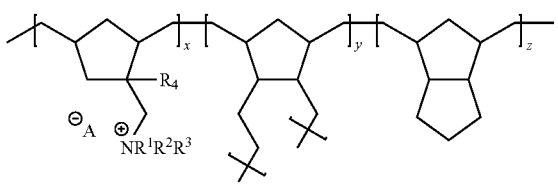

wherein $R^1$, $R^2$ and $R^3$ are, independently, a $C_1$ to $C_{20}$ group, wherein if the $C_1$ to $C_{20}$ group has a carbon in the beta position relative to the ammonium nitrogen atom then the beta carbon of the $C_1$ to $C_{20}$ group does not have a hydrogen substituent, wherein $R^4$ is a $C_1$ to $C_{20}$ group, wherein a first y unit is crosslinked to second y unit in a same or different ionomer chain than the first y unit, wherein $A^-$ is selected from halide, hydroxide, hexafluorophosphate, borate, carbonate, bicarbonate, and carboxylate, and wherein x is from 0.05 to 1, and x+y+z=1.

9. The ionomer of claim 6, wherein the ISOM and SOM units are connected by a carbon-carbon double bond and the ionomer has the following structure:

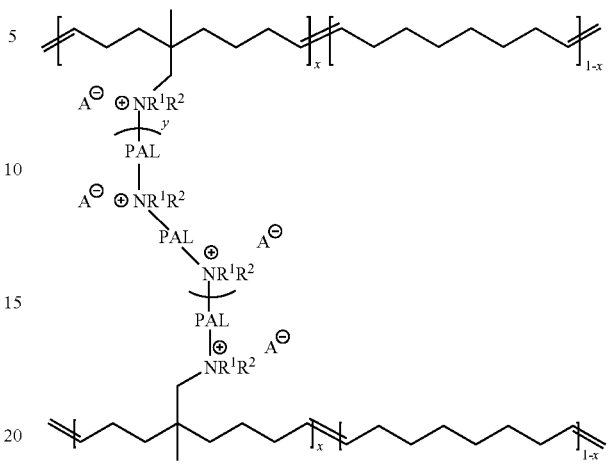

wherein $R^1$ and $R^2$ are, independently, a $C_1$ to $C_{20}$ group, wherein if the $C_1$ to $C_{20}$ group has a carbon in the beta position relative to the ammonium nitrogen atom then the beta carbon of the $C_1$ to $C_{20}$ group does not have a hydrogen substituent, wherein $A^-$ is selected from halide, hydroxide, hexafluorophosphate, borate, carbonate, bicarbonate and carboxylate, and wherein x is from 0.05 to 1, and wherein each PAL, independently, comprises a $C_1$ to $C_{20}$ group, wherein if the $C_1$ to $C_{20}$ group has a carbon in the beta position relative to the ammonium nitrogen atom then the beta carbon of the $C_1$ to $C_{20}$ group does not have a hydrogen substituent, and wherein y is from 0 to 20.

10. The ionomer of claim 9, wherein the ionomer has the following structure:

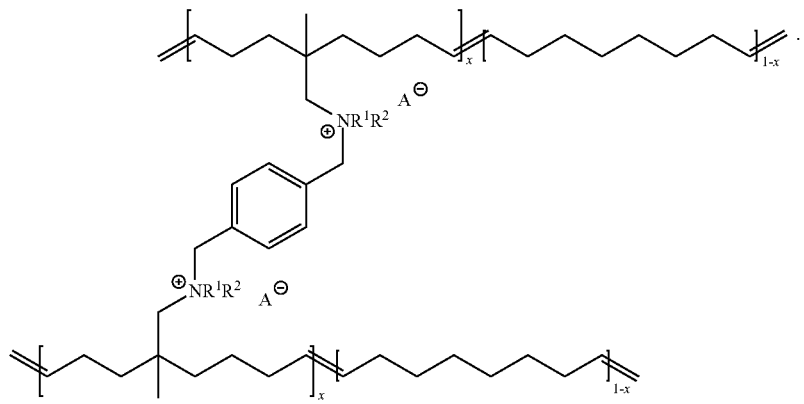

11. The ionomer of claim 1, wherein the ISOM and SOM units are connected by a carbon-carbon single bond and the ionomer has the following structure:

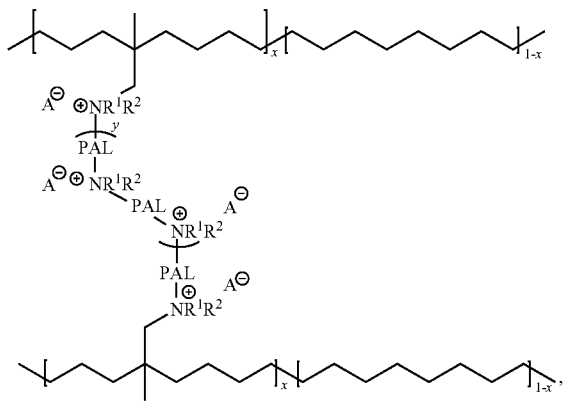

wherein $R^1$ and $R^2$ are, independently, a $C_1$ to $C_{20}$ group, wherein if the $C_1$ to $C_{20}$ group has a carbon in the beta position relative to the ammonium nitrogen atom then the beta carbon of the $C_1$ to $C_{20}$ group does not have a hydrogen substituent, wherein $A^-$ is selected from halide, hydroxide, hexafluorophosphate, borate, carbonate, bicarbonate and carboxylate, wherein x is from 0.05 to 1, and wherein each PAL or aliaromatic polyatomic linkage, independently, comprises a $C_1$ to $C_{20}$ group, wherein if the $C_1$ to $C_{20}$ group has a carbon in the beta position relative to the ammonium nitrogen atom then the beta carbon of the $C_1$ to $C_{20}$ group does not have a hydrogen substituent, and wherein y is from 0 to 20.

12. The ionomer of claim 11, wherein the ionomer has the following structure:

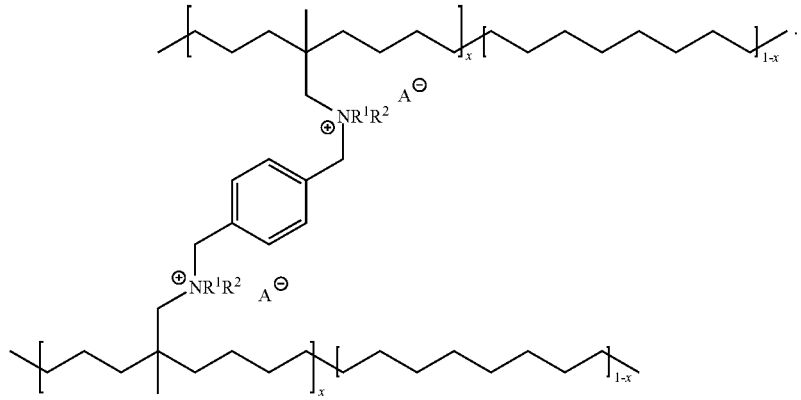

13. The ionomer of claim 1, wherein the ionomer is synthesized using a transition metal alkene polymerization catalyst, and wherein the ISOM and SOM units or the ISOM units are connected by a carbon-carbon double bond or carbon-carbon single bond.

14. The ionomer of claim 13, wherein the ROMP synthesis is carried out using a ruthenium-based metathesis catalyst.

15. The ionomer of claim 13, wherein at least 50% of the carbon-carbon double bonds linking the repeat units of the ionomer are reduced to carbon-carbon single bonds.

16. The ionomer of claim 13, wherein the ionomer is synthesized by a ring-opening methathesis polymerization (ROMP) carried out using a monomer comprising at least one tetraalkylammonium group having the following structure:

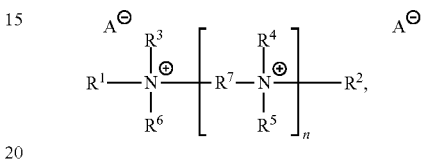

wherein $R^1$ is a $C_4$ to $C_{20}$ cycloalkenyl group and the carbon in the beta position relative to the ammonium nitrogen does not have a hydrogen substituent, wherein $R^2$, $R^3$, $R^4$, $R^5$ and $R^6$ are, independently, a $C_1$ to $C_{20}$ group, wherein if the $C_1$ to $C_{20}$ group has a carbon in the beta position relative to the ammonium nitrogen atom then the beta carbon of the $C_1$ to $C_{20}$ group does not have a hydrogen substituent, wherein each $R^7$ is independently a $C_1$ to $C_{20}$ group, wherein if the $C_1$ to $C_{20}$ group has a carbon in the beta position relative to the ammonium nitrogen atom then the beta carbon of the $C_1$ to $C_{20}$ group does not have a hydrogen substituent, wherein $A^-$ is selected from halide, hydroxide, hexafluorophosphate, borate, carbonate, bicarbonate and carboxylate, and wherein n is from 0 to 20.

17. The ionomer of claim 16, wherein the monomer is selected from the following structures:

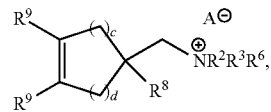

-continued

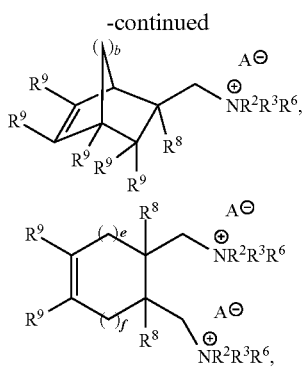

and combinations thereof, wherein $R^2$, $R^3$, $R^6$ are, independently, a $C_1$ to $C_{20}$ group, wherein if the $C_1$ to $C_{20}$ group has a carbon in the beta position relative to the ammonium nitrogen atom then the beta carbon of the $C_1$ to $C_{20}$ group does not have a hydrogen substituent, wherein each $R^8$ is a $C_1$-$C_{20}$ group, wherein each $R^9$ is independently selected from H and $C_1$ to $C_{20}$ group, wherein c and d are, independently, from 0 to 5, wherein b is 1 or 2, and wherein e and f are, independently, from 0 to 4.

18. The ionomer of claim 17, wherein the monomer is selected from the following structures:

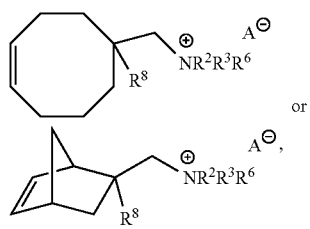

19. The ionomer claim 16, wherein the compound has the following structure:

Structure X

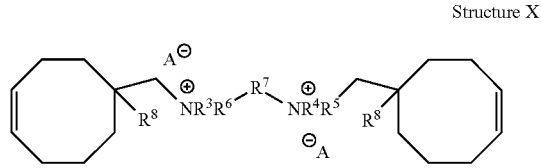

wherein $R^3$, $R^4$, $R^5$, $R^6$ are, independently, a $C_1$ to $C_{20}$ group, wherein if the $C_1$ to $C_{20}$ group has a carbon in the beta position relative to the ammonium nitrogen atom then the beta carbon of the $C_1$ to $C_{20}$ group does not have a hydrogen substituent, wherein each $R^8$ is a $C_1$-$C_{10}$ group, and wherein each $R^7$ is a polyatomic linking group and is comprised of a $C_1$ to $C_{20}$ group, wherein if the $C_1$ to $C_{20}$ group has a carbon in the beta position relative to the ammonium nitrogen atom then the beta carbon of the $C_1$ to $C_{20}$ group does not have a hydrogen substituent.

20. The ionomer of claim 19, wherein the compound has the following structure:

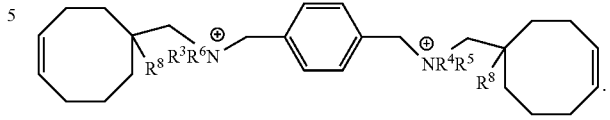

21. The ionomer of claim 16, wherein the ROMP synthesis is carried out using an additional monomer selected from the following structures:

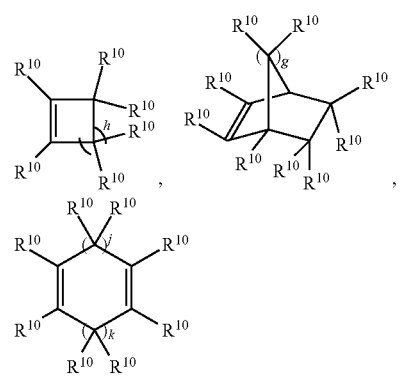

and combinations thereof, wherein each $R^{10}$ is independently selected from H and a $C_1$ to $C_{10}$ group, wherein h is from 1 to 10, wherein g is 1 or 2, and wherein j and k are, independently, from 0 to 5, except that j and k cannot both be 0 or both be 1.

22. The ionomer of claim 16, wherein the ROMP synthesis is carried out using an additional monomer selected from the following structures:

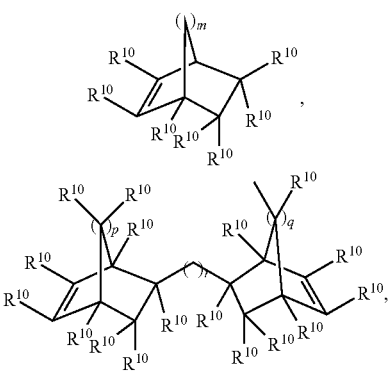

and combinations thereof, wherein each $R^{10}$ is independently selected from H and a $C_1$ to $C_{10}$ group, wherein m is 1 or 2, wherein p and q are, independently, 1 or 2, and r is from 1 to 20, wherein each s is, independently, from 0 to 5, and wherein n is from 0 to 20.

* * * * *